(12) United States Patent
Kanzaki et al.

(10) Patent No.: US 12,023,403 B2
(45) Date of Patent: Jul. 2, 2024

(54) OIL-IN-WATER TYPE EMULSION COSMETICS

(71) Applicant: DOW TORAY CO., LTD., Tokyo (JP)

(72) Inventors: Yasue Kanzaki, Ichihara (JP); Son Thanh Phan, Ichihara (JP); Jun Miyano, Tokyo (JP); Seiji Hori, Ichihara (JP)

(73) Assignee: DOW TORAY CO., LTD., Tokyo (JP)

( * ) Notice: Subject to any disclaimer, the term of this patent is extended or adjusted under 35 U.S.C. 154(b) by 194 days.

(21) Appl. No.: 17/267,940

(22) PCT Filed: Jul. 31, 2019

(86) PCT No.: PCT/JP2019/029956
§ 371 (c)(1),
(2) Date: Feb. 11, 2021

(87) PCT Pub. No.: WO2020/036064
PCT Pub. Date: Feb. 20, 2020

(65) Prior Publication Data
US 2021/0330571 A1    Oct. 28, 2021

(30) Foreign Application Priority Data
Aug. 15, 2018 (JP) .................. 2018-152804

(51) Int. Cl.
| A61K 8/892 | (2006.01) |
| A61K 8/06 | (2006.01) |
| A61K 8/27 | (2006.01) |
| A61K 8/29 | (2006.01) |
| A61K 8/81 | (2006.01) |
| A61Q 17/04 | (2006.01) |

(52) U.S. Cl.
CPC .............. *A61K 8/892* (2013.01); *A61K 8/062* (2013.01); *A61K 8/27* (2013.01); *A61K 8/29* (2013.01); *A61K 8/8147* (2013.01); *A61Q 17/04* (2013.01)

(58) Field of Classification Search
None
See application file for complete search history.

(56) References Cited

U.S. PATENT DOCUMENTS

| 4,501,619 | A | 2/1985 | Gee |
| 4,744,978 | A | 5/1988 | Homan et al. |
| 5,643,380 | A | 7/1997 | Saitoh et al. |
| 5,948,391 | A | 9/1999 | O'Lenick, Jr. |
| 6,384,104 | B1 | 5/2002 | Chang et al. |
| 7,981,405 | B2 | 7/2011 | Ueyama et al. |
| 8,500,900 | B2 | 8/2013 | Sugiura et al. |
| 8,900,553 | B2 | 12/2014 | Tamarkin et al. |
| 8,956,449 | B2 | 2/2015 | Kojima et al. |
| 9,486,652 | B2 | 11/2016 | Araki et al. |
| 10,130,579 | B2 | 11/2018 | Kanaya et al. |
| 2002/0031488 | A1 | 3/2002 | Kanji et al. |
| 2010/0189676 | A1 | 7/2010 | Matsuzawa et al. |
| 2010/0317555 | A1 | 12/2010 | Araki et al. |
| 2012/0251605 | A1 | 10/2012 | Iimura et al. |
| 2012/0263662 | A1 | 10/2012 | Iimura et al. |
| 2014/0199251 | A1 | 7/2014 | Ashida et al. |
| 2014/0235732 | A1 | 8/2014 | Ibe et al. |
| 2014/0348765 | A1 | 11/2014 | Sasaki |
| 2015/0011656 | A1 | 1/2015 | Tamura et al. |
| 2015/0216787 | A1 | 8/2015 | Hori et al. |
| 2015/0232601 | A1 | 8/2015 | Furukawa et al. |
| 2016/0120786 | A1 | 5/2016 | Halpern Chirch et al. |
| 2017/0035681 | A1 | 2/2017 | Kanaya et al. |
| 2018/0215877 | A1 | 8/2018 | Hori et al. |
| 2018/0263883 | A1 | 9/2018 | Uyama et al. |
| 2019/0053999 | A1 | 2/2019 | Hori et al. |
| 2019/0144612 | A1 | 5/2019 | Hori et al. |
| 2019/0231674 | A1 | 8/2019 | Furukawa et al. |
| 2021/0244641 | A1 | 8/2021 | Kondo et al. |
| 2021/0322296 | A1 | 10/2021 | Kikunaga et al. |
| 2021/0330559 | A1 | 10/2021 | Kondo et al. |
| 2021/0330571 | A1 | 10/2021 | Kanzaki et al. |
| 2022/0183955 | A1 | 6/2022 | Kondo et al. |

(Continued)

FOREIGN PATENT DOCUMENTS

| CN | 104125973 A | 10/2014 |
| EP | 2997956 A1 | 3/2016 |
| EP | 3132789 A1 | 2/2017 |

(Continued)

OTHER PUBLICATIONS

Machine assisted English translation of JP2002146189A obtained from https://patents.google.com/patent on May 26, 2022, 11 pages.
Momentive: "Silform INX fluid", Internet Citation, Feb. 2, 2015 (Feb. 2, 2015), XP002785508, Retrieved from the Internet: URL:http://www.essentialingredients.com/pdf/SilFormINXmarketingbrochure.pdf.
Database GNPD [Online] MINTEL; Oct. 29, 2012 (Oct. 29, 2012), anonymous: "Cream+", XP055907992, Database accession No. 1900229.
Database GNPD [Online] MINTEL; Apr. 22, 2016 (Apr. 22, 2016), anonymous: "Ultra Sun Protection Cream SPF 50+", XP055908000, Database accession No. 3945269.

(Continued)

*Primary Examiner* — Nannette Holloman
(74) *Attorney, Agent, or Firm* — WARNER NORCROSS + JUDD LLP

(57) ABSTRACT

Provided is an oil-in-water emulsion cosmetic composition having a high UV protection or blocking effect (particularly, boost effect of SPF value) and excellent water resistance and the like of a film (e.g., cosmetic film) without impairing the tactile sensation or the feeling of use particular to the oil-in-water emulsion cosmetic composition. The oil-in-water emulsion cosmetic composition comprises: (A) a carboxylic acid-modified silicone in a liquid form at 50° C., (B) a vinyl-based polymer emulsion, (C) a basic compound, and (D) an inorganic UV protecting agent consisting of hydrophobic fine particulate metal oxide. The oil-in-water emulsion cosmetic composition is useful as a sunscreen cosmetic composition.

16 Claims, No Drawings

(56) References Cited

U.S. PATENT DOCUMENTS

| | | | |
|---|---|---|---|
| 2022/0183956 A1 | 6/2022 | Kondo et al. | |
| 2022/0257497 A1 | 8/2022 | Kanzaki et al. | |

FOREIGN PATENT DOCUMENTS

| | | | |
|---|---|---|---|
| EP | 3213742 | A1 | 9/2017 |
| EP | 3327064 | A1 | 5/2018 |
| EP | 3838249 | A1 | 6/2021 |
| EP | 3838255 | A1 | 6/2021 |
| EP | 3838256 | A1 | 6/2021 |
| JP | S62103007 | A | 5/1987 |
| JP | H01261316 | A | 10/1989 |
| JP | H0844260 | A | 2/1996 |
| JP | H1143417 | A | 2/1999 |
| JP | 2001172463 | A | 6/2001 |
| JP | 2002146188 | A | 5/2002 |
| JP | 2002146189 | A | 5/2002 |
| JP | 2002275265 | A | 9/2002 |
| JP | 2002293726 | A | 10/2002 |
| JP | 2002322015 | A | 11/2002 |
| JP | 2004091423 | A | 3/2004 |
| JP | 2009185144 | A | 8/2009 |
| JP | 2011073971 | A | 4/2011 |
| JP | 2011148784 | A | 8/2011 |
| JP | 2011149017 | A | 8/2011 |
| JP | 2013144655 | A | 7/2013 |
| JP | 2013177370 | A | 9/2013 |
| JP | 2014040511 | A | 3/2014 |
| JP | 2014040512 | A | 3/2014 |
| JP | 2014201569 | A | 10/2014 |
| JP | 2015203026 | A | 11/2015 |
| JP | 2016185932 | A | 10/2016 |
| JP | 2017178930 | A | 10/2017 |
| JP | 2018024881 | | 2/2018 |
| JP | 2018115211 | A | 7/2018 |
| WO | 2013115099 | A1 | 8/2013 |
| WO | 2014185316 | A1 | 11/2014 |
| WO | 2015125332 | A1 | 8/2015 |
| WO | 2017018358 | A1 | 2/2017 |
| WO | 2017061090 | A1 | 4/2017 |
| WO | 2017191798 | A1 | 11/2017 |
| WO | 2018066559 | A1 | 4/2018 |
| WO | 2020036061 | A1 | 2/2020 |
| WO | 2020036062 | A1 | 2/2020 |
| WO | 2020036063 | A1 | 2/2020 |
| WO | 2020036064 | A1 | 2/2020 |
| WO | 2020036065 | A1 | 2/2020 |

OTHER PUBLICATIONS

Database GNPD [Online] MINTEL; Apr. 26, 2010 (Apr. 26, 2010), anonymous: "Skin Empowering Cream", XP055907993, Database accession No. 1323504.
Database GNPD [Online] MINTEL; Jan. 28, 2019 (Jan. 28, 2019), anonymous: "Wrinkle Resetter", XP055907996, Database accession No. 6296569.
Machine assisted English Translation of JPH01261316 obtained from https://worldwide.espacenet.com on May 3, 2021, 8 pages.
Machine assisted English Translation of JPH1143417 obtained from https://worldwide.espacenet.com on May 4, 2021, 13 pages.
Machine assisted English Translation of JP2002293726 obtained from https://worldwide.espacenet.com on May 3, 2021, 22 pages.
Machine assisted English Translation of JP2004091423 obtained from https://worldwide.espacenet.com on May 3, 2021, 14 pages.
Machine assisted English Translation of JP2011073971 obtained from https://worldwide.espacenet.com on May 3, 2021, 17 pages.
Machine assisted English Translation of JP2013177370 obtained from https://worldwide.espacenet.com on May 3, 2021, 18 pages.
Machine assisted English Translation of JP2014201569 obtained from https://worldwide.espacenet.com on May 3, 2021, 25 pages.
Machine assisted English Translation of JP2018115211 obtained from https://worldwide.espacenet.com on May 3, 2021, 41 pages.
Machine assisted English Translation of WO2013115099 obtained from https://worldwide.espacenet.com on May 3, 2021, 36 pages.
Machine assisted English Translation of WO2020036061 obtained from https://worldwide.espacenet.com on May 3, 2021, 40 pages.
Machine assisted English Translation of WO2020036062 obtained from https://worldwide.espacenet.com on May 3, 2021, 41 pages.
Machine assisted English Translation of WO2020036063 obtained from https://worldwide.espacenet.com on May 3, 2021, 34 pages.
Machine assisted English Translation of WO2020036064 obtained from https://worldwide.espacenet.com on May 3, 2021, 44 pages.
Machine assisted English Translation of WO2020036065 obtained from https://worldwide.espacenet.com on May 3, 2021, 37 pages.
English Translation of International Search Report for PCT/JP2019/029956, dated Oct. 8, 2019, 2 pages.
Momentive "SilForm™ INX Fluid"—Marketing Bulletin, obtained from https://www.momentive.com/docs/default-source/productdocuments/siliform-inx-fluid/siliform-inx-fluid-marketing-bulletin-(1).20956cf16e974c2d9a951e587eee27dc.pdf , 12 pages 2017.
English Translation of International Search Report for PCT/JP2019/029937, dated Oct. 21, 2019, 2 pages.
Cassiday www.aocs.org/stay-informed/inform-magazine/featured-articles/emulsions-making-oil-and-water-mix-april2014?SSO=True#(Year: 2014).
English Translation of International Search Report for PCT/JP2019/029930, dated Oct. 15, 2019, 2 pages.
English Translation of International Search Report for PCT/JP2019/029958, dated Oct. 15, 2019, 1 page.
English Translation of International Search Report for PCT/JP2019/029935, dated Oct. 15, 2019, 2 pages.
International Search Report for PCT/JP2019/029927 dated Oct. 15, 2019, 2 pages.
Machine assisted English translation of JP2017178930A obtained from https://worldwide.espacenet.com/patent on Dec. 15, 2023, 17 pages.
Machine assisted English translation of JP2016185932A obtained from https://worldwide.espacenet.com/patent on Dec. 15, 2023, 21 pages.
Machine assisted English translation of WO2015125332A1 obtained from https://worldwide.espacenet.com/patent on Dec. 15, 2023, 12 pages.
English translation of International Search Report for PCT/JP2019/029957 dated Oct. 8, 2019, 2 pages.
Machine assisted English translation of JP2002146188A obtained from https://worldwide.espacenet.com/patent on Dec. 11, 2023, 13 pages.
Machine assisted English translation of JP2002322015A obtained from https://worldwide.espacenet.com/patent on Dec. 11, 2023, 15 pages.
Machine assisted English Translation of JP2002275265A obtained from https://worldwide.espacenet.com/patent on May 2, 2023, 20 pages.

OIL-IN-WATER TYPE EMULSION COSMETICS

CROSS-REFERENCE TO RELATED APPLICATIONS

This application is the U.S. National Stage of International Application No. PCT/JP2019/029956 filed on 31 Jul. 2019, which claims priority to and all advantages of Japanese Application No. 2018-152804 filed on 15 Aug. 2018, the content of which is incorporated herein by reference.

TECHNICAL FIELD

The present invention relates to an oil-in-water emulsion cosmetic composition containing a continuous aqueous phase and a discontinuous oil phase and achieving a high UV protection effect.

BACKGROUND ART

Since the oil-in-water emulsion cosmetic composition containing an aqueous phase as a continuous phase gives a fresh and refreshing feeling of use, it has been widely used as a make-up cosmetic composition such as a base cosmetic composition such as emulsion, a foundation cosmetic composition, a sunscreen agent, foundation, or eye shadow. In particular, an oil-in-water emulsion cosmetic composition containing an inorganic UV protecting agent typified by hydrophobic fine particulate titanium oxide and hydrophobic fine particulate zinc oxide can be designed to have a high SPF (=Sun Protection Factor) value, which is an index showing the degree of an effect of blocking UV-B waves (wavelength 280 to 315 nm) among ultraviolet rays, and thus has been widely used as a sunscreen cosmetic composition such as sunscreen.

Further, the oil-in-water emulsion cosmetic composition has a problem in that a cosmetic film obtained by applying the cosmetic composition is usually inferior in water resistance, and thus, for the purpose of imparting water resistance to the cosmetic film, Patent Document 1 proposes to compound a hydrophobic powder such as hydrophobic fine particulate titanium oxide and hydrophobic fine particulate zinc oxide. Furthermore, in Patent Document 2, it has been proposed to use carboxylic acid-modified silicone under alkaline conditions in order to favorably disperse the hydrophobic powder in the aqueous phase and stabilize the cosmetic composition. However, these documents do not disclose or suggest a method for improving the UV protection property (particularly, SPF value) derived from the hydrophobic fine particulate titanium oxide, the hydrophobic fine particulate zinc oxide, and the like.

On the other hand, in recent years, sunscreen cosmetic compositions with high UV protection property have been required, and the SPF value, which is an index, is dependent on the compounding amount of inorganic UV protecting agent such as hydrophobic fine particulate titanium oxide, hydrophobic fine particulate zinc oxide, and the like. Therefore, it is necessary to add a large amount of these inorganic powders to cosmetic compositions to achieve a high SPF value. However, when a large amount of these inorganic UV protecting agents are added to the oil-in-water emulsion cosmetic composition, the feeling of use peculiar to the oil-in-water emulsion cosmetic composition may be impaired, which may cause powderiness or roughness. For this reason, it has been extremely difficult to achieve a film performance that has both fresh and refreshing feeling of use peculiar to the oil-in-water emulsion cosmetic composition and a high SPF value, and high water resistance.

On the other hand, vinyl-based polymers such as acrylic acid/methacrylic acid copolymer polymers (including those modified by a carbosiloxane structure) and emulsions thereof have been widely used as materials for cosmetic compositions such as film forming agents, and sunscreen cosmetic compositions such as sunscreens including the same have also been proposed (for example, Patent Documents 3 to 5). However, these documents do not disclose or suggest a method for improving the UV protection property (particularly, SPF value) derived from inorganic UV protecting components such as the hydrophobic fine particulate titanium oxide, the hydrophobic fine particulate zinc oxide, and the like, by using vinyl-based polymer emulsion and carboxylic acid-modified silicone together, or by combining specific components.

RELATED ART DOCUMENTS

Patent Documents

Patent Document 1: Japanese Unexamined Patent Application Publication No. 2004-91423
Patent Document 2: Japanese Unexamined Patent Application Publication No. 2015-203026
Patent Document 3: US Patent Application Publication No. 2016-120786
Patent Document 4: PCT International Publication No. 2017/061090
Patent Document 5: Japanese Unexamined Patent Application Publication No. 2001-172463

SUMMARY OF THE INVENTION

Problem to be Solved by the Invention

The present invention has been made to solve the problems described above, and an object of the present invention is to provide an oil-in-water emulsion cosmetic composition having a high SPF value and excellent in water resistance and the like of a film (cosmetic film) without impairing the tactile sensation or the feeling of use peculiar to the oil-in-water emulsion cosmetic composition.

Similarly, an object of the present invention is to provide an oil-in-water emulsion cosmetic composition that further improves UV protection property (in particular, an SPF value) derived from inorganic UV protecting components such as hydrophobic fine particulate titanium oxide, hydrophobic fine particulate zinc oxide, and the like in the oil-in-water emulsion cosmetic composition to give a sufficient SPF value as a whole cosmetic composition even if the compounding amount of these components is suppressed.

Means for Solving the Problem

As a result of diligent examination to solve the above problems, the present inventors have reached the present invention by discovering an oil-in-water emulsion cosmetic composition contains (A) carboxylic acid-modified silicone in a liquid form at 50° C., (B) a vinyl-based polymer emulsion, (C) a basic compound, and (D) an inorganic UV protecting agent consisting of hydrophobic fine particulate metal oxide. In particular, when the component (A) and the component (B) described above are used in combination in the oil-in-water emulsion cosmetic composition, a UV protection effect derived from the component (D), particularly, the SPF value is improved, and a high SPF value is achieved as a whole cosmetic composition even if the compounding amount of the component (D) is suppressed, as compared to a case where these components are not contained.

In other words, an object of the present invention is achieved by:

[1] An oil-in-water emulsion cosmetic composition containing (A) carboxylic acid-modified silicone in a liquid form at 50° C.;
(B) a vinyl-based polymer emulsion;
(C) a basic compound; and
(D) an inorganic UV protecting agent consisting of hydrophobic fine particulate metal oxide.

Further preferably, an object of the present invention is achieved by:

[2] The oil-in-water emulsion cosmetic composition according to [1], wherein for 100 parts by mass of the (D) inorganic UV protecting agent consisting of hydrophobic fine particulate metal oxide,
the (A) carboxylic acid-modified silicone in a liquid form at 50° C. is in an amount in a range of 5 to 40 parts by mass of,
the (B) vinyl-based polymer emulsion is in an amount in a range such that a content of solid content in the emulsion is 0.5 to 10 parts by mass, and
the SPF value of the whole cosmetic composition is improved compared to a case where the component (A) and the component (B) are not contained.

More preferably, the object of the present invention is achieved by the following oil-in-water emulsion cosmetic composition.

[3] The oil-in-water emulsion cosmetic composition according to [1] or [2], wherein the (A) carboxylic acid-modified silicone is represented by the following structural formula (1):

[Formula 1]

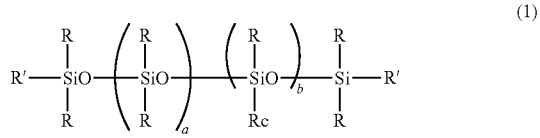

(1)

(wherein:
Rc represents a carboxyl group-containing organic group represented by a general formula: —$R^1$—($OR^2$)p-(O)w-$R^3$—COOH, ($R^1$ represents a linear or branched alkylene group having 2 to 22 carbon atoms, $R^2$ represents a linear or branched alkylene group having 2 to 4 carbon atoms, $R^3$ represents a bond (—) or a linear or branched alkylene group having 1 to 22 carbon atoms, p represents a number from 0 to 200, and w represents a number of 0 or 1),
R represents the same or different alkyl or alkoxy group, having 1 to 22 carbon atoms, or phenyl group,
R' is Rc or R, and
a and b are 0 or positive numbers, respectively, a+b is a number in a range of 0 to 30, and when b is 0, at least one of R' is Rc).

[4] The oil-in-water emulsion cosmetic composition according to any one of [1] to [3], wherein the (A) carboxylic acid-modified silicone is in a liquid form at room temperature (25° C.).

[5] The oil-in-water emulsion cosmetic composition according to any one of [1] to [4], wherein the (A) carboxylic acid-modified silicone is represented by the following structural formula (2):

[Formula 2]

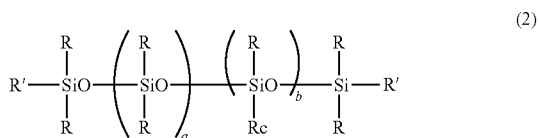

(2)

(wherein:
Rc represents a carboxyl group-containing organic group represented by a general formula: —$R^1$—($OR^2$)p-(O)w-$R^3$—COOH, ($R^1$ represents a linear or branched alkylene group having 2 to 22 carbon atoms, $R^2$ represents a linear or branched alkylene group having 2 to 4 carbon atoms, $R^3$ represents a bond (—) or a linear or branched alkylene group having 1 to 22 carbon atoms, p represents a number from 0 to 200, and w represents a number of 0 or 1),
R represents the same or different alkyl or alkoxy group, having 1 to 22 carbon atoms, or phenyl group,
R' is Rc or R, and
each of a and b is a positive number, a+b is a number in a range of 2 to 20, and a/b is in a range of 0.3 to 3.0).

[6] The oil-in-water emulsion cosmetic composition according to any one of [1] to [5], wherein the (A) carboxylic acid-modified silicone is contained in a range of 0.5% to 15% by mass with respect to a total mass of the cosmetic composition.

[7] The oil-in-water emulsion cosmetic composition according to any one of [1] to [6], wherein the vinyl-based polymer emulsion (B) is an emulsion of an acrylic copolymer polymer obtained by copolymerizing an acrylate ester monomer or a methacrylate monomer.

[8] The oil-in-water emulsion cosmetic composition according to any one of [1] to [7], wherein the (B) vinyl-based polymer emulsion is an emulsion of one or more types of acrylic copolymer polymers selected from:
(b1) an acrylic acid/alkyl methacrylate copolymer polymer,
(b2) an acrylic acid/styrene methacrylate copolymer polymer, and
(b3) an acrylic acid/methacrylic acid copolymer polymer having a carbosiloxane dendron structure.

[9] The oil-in-water emulsion cosmetic composition according to any one of [1] to [8], wherein the (D) inorganic UV protecting agent consisting of hydrophobic fine particulate metal oxide is hydrophobic fine particulate titanium oxide or hydrophobic fine particulate zinc oxide having an average particle size in the range of 1 to 200 nm.

[10] The oil-in-water emulsion cosmetic composition according to any one of [1] to [9], further containing (E) an oil agent.

[11] The oil-in-water emulsion cosmetic composition according to [10], wherein the (E) oil agent contains at least one type of UV absorber.

[12] The oil-in-water emulsion cosmetic composition according to any one of [1] to [11], further containing (F) an oil-soluble film forming agent.

[13] The oil-in-water emulsion cosmetic composition according to any one of [1] to [12], further containing (G) polyhydric alcohol.

[14] The oil-in-water emulsion cosmetic composition according to any one of [1] to [13], further containing (H) a water-soluble UV absorber.

[15] The oil-in-water emulsion cosmetic composition according to any one of [1] to [14], which is a sunscreen cosmetic composition.

Effects of the Invention

The cosmetic composition of the present invention has improved UV protection property (in particular, SPF values) derived from inorganic UV protecting components such as hydrophobic fine particulate titanium oxide, hydrophobic fine particulate zinc oxide, and the like, and has a high SPF value as a whole cosmetic composition without impairing the tactile sensation or the feeling of use peculiar to the oil-in-water emulsion cosmetic composition. In other words, in the oil-in-water emulsion cosmetic composition of the present invention, by boosting the SPF value derived from the inorganic UV protecting component, which is a hydrophobic powder, in specific combinations of the other components, it is possible to achieve both the UV protection property derived from the inorganic UV protecting component, which is originally in a trade-off relationship, and the feeling of use peculiar to the oil-in-water emulsion cosmetic composition at a high level. Therefore, by utilizing the present invention, it is possible to provide a sunscreen cosmetic composition or the like that has an increased degree of freedom in formulation design, and has both a fresh and refreshing feeling of use and the UV protection property typified by the SPF value.

Furthermore, the cosmetic composition of the present invention has excellent stability in terms of maintaining uniform appearance without causing phase separation over time, and also significantly exhibits excellent water resistance of the film (cosmetic film).

In addition, since the cosmetic composition of the present invention contains the component (A) and the component (C), the formed cosmetic film has the advantage in that it can be easily removed by using normal soap and water.

PREFERRED MODE FOR CARRYING OUT THE INVENTION

Hereinafter, an oil-in-water emulsion cosmetic composition of the present invention will be described in detail.

One of the main technical effects of the present invention is, in an oil-in-water emulsion cosmetic composition containing (D) an inorganic UV protecting agent consisting of hydrophobic fine particulate metal oxide, to further improve the UV protection property (in particular, the SPF value) derived from the inorganic UV protecting component, which is a hydrophobic powder, as a whole cosmetic composition by using (A) carboxylic acid-modified silicone in a liquid form at 50° C., (B) a vinyl-based polymer emulsion, and (C) a basic compound in combination. In the present invention, the improving effect of the SPF value may be expressed as "boosting/causing the SPF value of the cosmetic composition to be boosted".

[(A) Carboxylic Acid-Modified Silicone]

The cosmetic composition of the present invention contains at least one type of (A) carboxylic acid-modified silicone in a liquid form at 50° C. Note that, the (A) carboxylic acid-modified silicone may be in a liquid form at room temperature 50° C. and one atmosphere, and for example, it may be a solid at room temperature (25° C.).

In the present invention, the carboxylic acid-modified silicone is a component that functions as a surfactant, and, at the same time, is a component that improves the UV protection property (in particular, the SPF value) derived from the inorganic UV protecting component that is a hydrophobic powder by using the (B) vinyl-based polymer emulsion. When the carboxylic acid-modified silicone is not used, the effect of boosting the SPF value of the cosmetic composition from the (B) vinyl-based polymer emulsion is insufficient, and it may not be possible to achieve both the UV protection property derived from the inorganic UV protecting component and the feeling of use peculiar to oil-in-water emulsion cosmetic composition. On the other hand, when the (A) carboxylic acid-modified silicone is used alone, the effect of boosting the SPF value of the cosmetic composition is limited, and the effect of boosting the SPF value by combining the two is sufficiently exhibited.

The carboxylic acid-modified silicone contained in the cosmetic composition of the present invention is not particularly limited as long as it is an organosiloxane in which at least one carboxyl group-containing organic group is introduced to a side chain or an end, as long as the carboxylic acid-modified silicone is in a liquid form at 50° C. Preferably, the carboxyl group-containing organic group is introduced into the side chain of the organosiloxane.

Therefore, examples of the carboxylic acid-modified silicone include those in which a silicone main chain is grafted with a carboxyl group-containing organic group; a carboxyl group-containing organic group is added to one end of the silicone main chain; a carboxyl group-containing organic group is added to both ends of the silicone main chain; a carboxyl group-containing organic group is added to both ends of the silicone main chain, and the carboxyl group-containing organic group is further grafted; a silicone main chain grafted with a silicone chain (including a siloxane macromonomer bonded by a silalkylene bond) and a carboxyl group-containing organic group; and a silicone main chain or the end has a siloxane modifying group having a carbosiloxane dendrimer structure and a carboxyl group-containing organic group, and optionally, carboxylic acid-modified silicone having a long-chain alkyl group having 6 or more carbon atoms can be exemplified. The carboxylic acid-modified silicone in which a silicone main chain is grafted with a carboxyl group-containing organic group is most suitable. Note that, when the carboxylic acid-modified silicone has a long chain alkyl group, compounding stability with an organic oil agent such as hydrocarbon oil or an organic material for a cosmetic composition (in particular, UV absorber) may be improved.

A linking group may be present between a carboxyl group and a silicon atom, and examples of the linking group include divalent or higher valent organic groups such as an alkylene group which may have a hetero atom and a polyoxyalkylene group, but are not particularly limited. Furthermore, the (n−1) carboxyl group may be carboxylic acid-modified silicone bonded to a silicon atom by an n-valent linking group (n is a number of equal to or larger than 3). Specifically, the silicone having a carboxyl group on the main chain or side chain of the silicone via the following linking group is included in the carboxylic acid-modified silicone of the present invention.

Organopolysiloxane having a silicon-bonded carboxyl group-containing organic group as disclosed in Japanese Translation of PCT International Application Publication No. 11-504665:

[Formula 3]

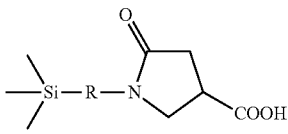

(wherein, R represents a $C_1$-$C_{12}$ alkylene group, a $C_1$-$C_{12}$ alkyleneoxy group, an oxygen atom, a sulfur atom, —NH—, or —NR'— (R' is a $C_1$-$C_6$ alkyl group), or a divalent group containing a combination of these), Organopolysiloxane having any of the following carboxyl group-containing organic groups, disclosed in Japanese Unexamined Patent Application Publication No. 2002-114849:

[Formula 4]

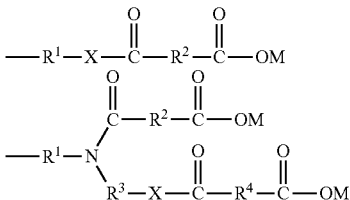

(wherein, $R^1$ to $R^{24}$ represent linear or branched chain alkylene groups, alkenylene groups, or arylene groups having 2 to 22 carbon atoms, which are the same or different and may have a substituent containing a hetero atom, X represents —O— or NH—, and M represents a hydrogen atom), Organopolysiloxane having a carboxyl group-containing organic group disclosed in Japanese Translation of PCT International Application Publication No. 2005-524747:

[Formula 5]

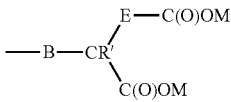

(wherein B represents an alkylene residue substituted with one or more alkyl groups having 2 to 30 carbon atoms and optionally 1 to 30 carbon atoms, R' represents a hydrogen atom or an alkyl group having 1 to 30 carbon atoms, E is an alkylene residue that is absent or is substituted with one or more alkyl groups having 1 to 5 carbon atoms, preferably 1 to 3 carbon atoms, and optionally 1 to 30 carbon atoms; and M is a hydrogen atom), Organopolysiloxane having the following carboxyl group-containing organic group represented by the following average composition formula, disclosed in Japanese Unexamined Patent Application Publication No. 2009-263643:

[Formula 6]

[wherein, $R^1$ is a group selected from an alkyl group having 1 to 30 carbon atoms, a phloroalkyl group having 1 to 30 carbon atoms, an aryl group having 6 to 30 carbon atoms, and an aralkyl group having 6 to 30 carbon atoms, $R^2$ is a group represented by Formula (2) below, and when c is 0, $R^2$ is bonded to at least one end of the organopolysiloxane

[Formula 7]

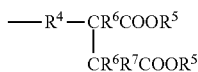

(wherein $R^4$ is a divalent hydrocarbon group having or not having an oxygen atom having 2 to 20 carbon atoms, $R^5$ is a hydrogen atom, $R^6$s each independently represent a hydrogen atom or an alkyl group having 1 to 6 carbon atoms, and $R^7$ is a hydrogen atom or an alkyl group having 1 to 6 carbon atoms), $R^3$ is a group represented by Formula (3) below:

[Formula 8]

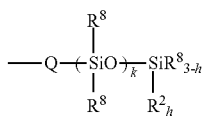

(wherein, $R^2$ is as described above, $R^8$s each independently represent the group selected from an alkyl group having 1 to 30 carbon atoms, a fluoroalkyl group having 1 to 30 carbon atoms, an aryl group having 6 to 30 carbon atoms, and an aralkyl group having 6 to 30 carbon atoms, Q is $C_dH_{2d}$ (here, d is an integer of 1 to 5, preferably an integer of 2 to 4) or an oxygen atom, k is an integer of 0 to 500, preferably 1 to 100, and more preferably 5 to 60, and h is an integer of 0 to 3 and preferably 0).

Particularly suitable examples of the carboxylic acid-modified silicone used in the present invention include carboxylic acid-modified silicone in which at least one silicon atom on the side chain or the end of the silicone main chain is bonded to a carboxyl group-containing organic group represented by a general formula: —$R^1$—($OR^2$)p-(O)w-$R^3$—COOH, (wherein, $R^1$ represents a linear or branched alkylene group having 2 to 22 carbon atoms, $R^2$ represents a linear or branched alkylene group having 2 to 4 carbon atoms, $R^3$ represents a bond (—) or a linear or branched alkylene group having 1 to 22 carbon atoms, p represents a number from 0 to 200, and w represents a number of 0 or 1).

In the general formula representing the carboxyl group-containing organic group, $R^1$ is a linear or branched alkylene group having 2 to 22 carbon atoms, preferably a linear alkylene group having 2 to 12 carbon atoms, and particularly preferably a linear alkylene group having 2 to 10 carbon atoms. Examples thereof include ethylene, propylene, trimethylene, butylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups.

In addition, examples of the linear or branched alkylene group having 2 to 4 carbon atoms of $R^2$ include ethylene, propylene, trimethylene and butylene groups, and an ethylene group is particularly preferable.

Examples of the linear or branched alkylene group having 1 to 22 carbon atoms of $R^3$ include ethylene, ethylethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups. Among these, those having 1 to 12 carbon atoms, particularly those in which the sum of the carbon atoms of $R^1$ and $R^3$ is 2 to 22 are preferable.

p represents the number of 0 to 200, and the number of 0 to 20 is preferable, and the number of 0 to 10 is particularly preferable. In addition, w represents the number of 0 or 1, and is preferably 0. Note that, when p and w are both 0, the carboxyl group-containing organic group is represented by the structural formula —$(C_nH_{2n})$—COOH, and the carboxyl group-containing organic group preferably has a structure in which one carboxyl group is bonded to a silicon atom via a linear or branched alkylene group having 3 to 44 carbon atoms. In the formula, n is a number of 3 to 44, preferably a number of 3 to 20, and particularly preferably a number of 3 to 16.

Examples of the carboxylic acid-modified silicone used in the present invention include organopolysiloxane represented by the following structural formula (1):

[Formula 9]

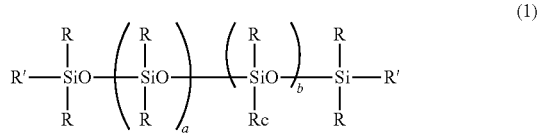

(1)

(wherein Rc represents a carboxyl group-containing organic group represented by a general formula: —$R^1$—$(OR^2)p$-$(O)w$-$R^3$—COOH, R represents the same or different alkyl or alkoxy group, having 1 to 22 carbon atoms, or phenyl group, R' is Rc or R, and each of a and b is a number in the range of 0 or more, and a+b is a number in the range of 0 to 1000. here, when b=0, at least one of R' is Rc). In particular, the carboxylic acid-modified silicone disclosed in Japanese Unexamined Patent Application Publication No. 8-109263 and some of (other than those having a siloxane dendron structure) of the carboxylic acid-modified silicone disclosed in PCT International Publication No. WO 2009/22621 are represented by the structural formula (1) and are included in the carboxylic acid-modified silicone suitably used in the present invention.

Suitable examples of the carboxylic acid-modified silicone represented by structural formula (1) include carboxylic acid-modified silicone in which a+b is a number in the range 0 to 500, particularly, b>0, and a carboxyl group-containing organic group represented by the general formula: —$R^1$—$(OR^2)p$-$(O)w$-$R^3$—COOH is grafted with the silicone main chain, and carboxylic acid-modified silicone in which b=0, and R' at both ends of the silicone main chain is a carboxyl group-containing organic group represented by the general formula: —$R^1$—$(OR^2)p$-$(O)w$-$R^3$—COOH. In the present invention, particularly suitable carboxylic acid-modified silicone is carboxylic acid-modified silicone having a large number of carboxyl group-containing organic groups in the side chain moiety, and it is preferable that b>a, and it is more suitable that b>0 and a=0. "b>a" means that more than half of the side chain moieties have siloxane units having a carboxyl group-containing organic group, and a+b is preferably a number in the range of 1 to 500. Furthermore, when a=0, if b>0, all of the siloxane units in the side chain moiety having a carboxyl group-containing organic group, and b is most preferably a number in a range of 1 to 200 or a number in a range of 1 to 50.

In structural formula (1), R is preferably a methyl group, an alkoxy group, or a phenyl group, but from the viewpoint of compounding stability with an organic oil agent such as a hydrocarbon oil or an organic material for a cosmetic composition (in particular, a UV absorber), R may have a long chain alkyl group with 6 to 22 carbon atoms in a part. A degree of modification by the carboxyl group-containing organic group is not particularly limited, and if a+b is a number in the range of 0 to 500, it is preferable to have an average of 2 to 100 of the carboxyl group-containing organic groups in the molecule, including a case where the carboxyl group-containing organic group is bonded to both ends of the silicone main chain.

In the present invention, such carboxylic acid-modified silicone can be manufactured by known methods such as a method of subjecting dimethylpolysiloxane having a Si—H group and an unsaturated carboxylic acid ester compound to addition reaction under a platinum catalyst and to saponification to form carboxylic acid; a method of subjecting dimethylpolysiloxane having a Si—H group to addition reaction of unsaturated carboxylic acid silyl ester or allyloxycarboxylic acid silyl ester under a platinum catalyst to obtain the desired product by hydrolysis after the reaction; and a method of obtaining carboxylic acid-modified silicone at both ends by an equilibrium reaction using bis(hydroxycarbonylethyl) tetramethyldisiloxane with cyclic siloxane and an acidic catalyst (Silicone Handbook, edited by Kunio Ito, NIKKAN KOGYO SHIMBUN, LTD. pp. 166-167).

Further, in the present invention, as the carboxylic acid-modified silicone represented by the structural formula (1), commercially available carboxylic acid-modified silicone can be used as it is or after removing the solvent. Specific examples thereof include BY16-880, BY16-750, and FZ-3516 (available from Dow Toray Co., Ltd.), TSF 4770, and TSF 4771 (available from Momentive Performance Materials), X-22-162A, X-22-162C, X-22-3701 E, and X-22-3710 (available from Shin-Etsu Chemical Co., Ltd.), and the like.

From the viewpoint of technical effects of the present invention, the (A) carboxylic acid-modified silicone is preferably in a liquid form at room temperature (25° C.). Note that, the (A) carboxylic acid-modified silicone may be in a liquid form at room temperature (25° C.) and one atmosphere. This is because the carboxylic acid-modified silicone that is in a liquid form at room temperature (25° C.) functions as a surfactant and is easy to mix with the vinyl-based polymer emulsion, which is component (B).

The (A) carboxylic acid-modified silicone is more preferably represented by the following structural formula (2):

[Formula 10]

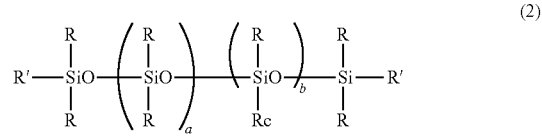

(2)

(wherein:
Rc represents a carboxyl group-containing organic group represented by a general formula: —$R^1$—$(OR^2)p$-$(O)w$-$R^3$—COOH, ($R^1$ represents a linear or branched alkylene group having 2 to 22 carbon atoms, $R^2$ represents a linear or branched alkylene group having 2 to 4 carbon atoms, $R^3$ represents a bond (—) or a linear or branched alkylene group having 1 to 22 carbon atoms, p represents a number from 0 to 200, and w represents a number of 0 or 1), R represents the same or different alkyl or alkoxy group or phenyl group having 1 to 22 carbon atoms, R' is Rc or R, and each of a and b is a positive number, a≥2 is preferable, and b≥2 is preferable, a+b is a number in the range of 2 to 20, preferably 2 to 15, and more preferably 2 to 10, and a/b is in the range of 0.3 to 3.0, preferably 0.3 to 2.5, more preferably 0.3 to 2.0, and even more preferably 0.5 to 2.0).

In the general formula representing the carboxyl group-containing organic group in the structural formula (2), $R^1$ is a linear alkylene group having 2 to 22 carbon atoms, preferably a linear alkylene group having 2 to 12 carbon atoms, and particularly preferably a linear alkylene group having 2 to 10 carbon atoms. Examples thereof include ethylene, propylene, trimethylene, butylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups.

In addition, examples of the linear or branched alkylene group having 2 to 4 carbon atoms of $R^2$ include ethylene, propylene, trimethylene and butylene groups, and an ethylene group is particularly preferable.

Examples of the linear or branched alkylene group having 1 to 22 carbon atoms of $R^3$ include ethylene, ethylethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups. Among these, those having 1 to 12 carbon atoms, particularly those in which the sum of the carbon atoms of $R^1$ and $R^3$ is 2 to 22 are preferable.

p represents the number of 0 to 200, and the number of 0 to 20 is preferable, and the number of 0 to 10 is particularly preferable. In addition, w represents the number of 0 or 1, and is preferably 0. Note that, when p and w are both 0, the carboxyl group-containing organic group is represented by the structural formula —$(C_nH_{2n})$—COOH, and the carboxyl group-containing organic group preferably has a structure in which one carboxyl group is bonded to a silicon atom via a linear or branched alkylene group having 3 to 44 carbon atoms. In the formula, n is a number of 3 to 44, preferably a number of 3 to 20, and particularly preferably a number of 3 to 16.

The (A) carboxylic acid-modified silicone represented by structural formula (2) is not particularly limited as long as the at least one carboxyl group-containing organic group is a side chain or the end introduced organosiloxane. Preferably, the carboxyl group-containing organic group is introduced into the side chain of the organosiloxane.

Therefore, examples of the (A) carboxylic acid-modified silicone represented by the structural formula (2) include those in which a silicone main chain is grafted with a carboxyl group-containing organic group as a side chain; a carboxyl group-containing organic group is added to one end of the silicone main chain; a carboxyl group-containing organic group is added to both ends of the silicone main chain; and a carboxyl group-containing organic group is added to both ends of the silicone main chain, and the carboxyl group-containing organic group is further grafted as a side chain; and optionally, carboxylic acid-modified silicone having a long-chain alkyl group having 6 or more carbon atoms can be exemplified. The carboxylic acid-modified silicone in which a silicone main chain is grafted with a carboxyl group-containing organic group is most suitable as a side chain. Note that, when the carboxylic acid-modified silicone has a long chain alkyl group, compounding stability with an organic oil agent such as hydrocarbon oil or an organic material for a cosmetic composition (in particular, UV absorber) may be improved.

The (A) carboxylic acid-modified silicone represented by the structural formula (2) is preferably carboxylic acid-modified silicone in which R' is R and a carboxyl group-containing organic group represented by the general formula: —$R^1$—$(OR^2)p$-$(O)w$-$R^3$—COOH is grafted with the silicone side chain; more preferably carboxylic acid-modified silicone in which R' is R and the silicone side chain has a plurality of the aforementioned carboxyl group-containing organic groups; and still more preferably carboxylic acid-modified silicone in which R' is R, the silicone side chain has a plurality of the aforementioned carboxyl group-containing organic groups, and a/b=1.

In structural formula (2), R is preferably a methyl group, an alkoxy group, or a phenyl group, but from the viewpoint of compounding stability with an organic oil agent such as a hydrocarbon oil or an organic material for a cosmetic composition (in particular, a UV absorber), R may have a long chain alkyl group with 6 to 22 carbon atoms in a part.

In the present invention, such carboxylic acid-modified silicone can be manufactured by known methods such as a method of subjecting dimethylpolysiloxane having a Si—H group and an unsaturated carboxylic acid ester compound to addition reaction under a platinum catalyst and to saponification to form carboxylic acid; a method of subjecting dimethylpolysiloxane having a Si—H group to addition reaction of unsaturated carboxylic acid silyl ester or allyloxycarboxylic acid silyl ester under a platinum catalyst to obtain the desired product by hydrolysis after the reaction; and a method of obtaining carboxylic acid-modified silicone at both ends by an equilibrium reaction using bis(hydroxycarbonylethyl) tetramethyldisiloxane with cyclic siloxane and an acidic catalyst (Silicone Handbook, edited by Kunio Ito, NIKKAN KOGYO SHIMBUN, LTD. pp. 166-167). Furthermore, particularly, examples of the suitable carboxylic acid-modified silicone of the present invention include those available from the trade name ES-5800 Formulation Aid (available from Dow Toray Co., Ltd.), and the like.

In the oil-in-water emulsion cosmetic composition of the present invention, the (A) carboxylic acid-modified silicone is preferably contained in a range of 0.5% to 15% by mass, more preferably in a range of 1.0% to 10% by mass, and still more preferably in a range of 1.5% to 7.5% by mass, based on the total mass of the cosmetic composition.

In the oil-in-water emulsion cosmetic composition of the present invention, in order to boost the SPF value of the cosmetic composition, the (A) carboxylic acid-modified silicone is preferably contained in an amount in the range of 5 to 40 parts by mass, and particularly preferably in an amount in the range of 7.5 to 35 parts by mass, with respect to 100 parts by mass of an (D) inorganic UV protecting agent consisting of hydrophobic fine particulate metal oxide described later. In the range described above, the component (D) is stably dispersed in the aqueous phase by the (A) carboxylic acid-modified silicone to provide a film (=cosmetic film) having good water resistance and when using it in combination with the component (B), the effect of improving the SPF value of the whole cosmetic composition is excellent.

On the other hand, when the oil-in-water emulsion cosmetic composition of the present invention uses a small amount of a surfactant other than the (A) carboxylic acid-modified silicone or does not contain other surfactants, the water resistance of the cosmetic film obtained by the cosmetic composition of the present invention can be further enhanced in some cases. For example, when the content of the surfactant other than the (A) carboxylic acid-modified silicone is less than 5% by mass of the total mass of the cosmetic composition, the water resistance of the cosmetic film may be further improved due to the combination with the hydrophobic powder, which is the component (D). In particular, from the perspective of improving the water resistance of the cosmetic film, the content of the surfactant other than the (A) carboxylic acid-modified silicone is advantageously low, preferably 3% by mass or less, more preferably 2% by mass or less, and still more preferably 1% by mass or less. The cosmetic composition of the present invention is most preferably free of any surfactant other than the (A) carboxylic acid-modified silicone.

[(B) Vinyl-Based Polymer Emulsion]

The cosmetic composition of the present invention contains a vinyl-based polymer emulsion such as an acrylic acid/methacrylic acid copolymer polymer. The vinyl-based polymer is a film forming component or a water-based thickener that forms a cosmetic film on the skin or the like, and is a component that improves the UV protection property (in particular, the SPF value) derived from an inorganic UV protecting component that is a hydrophobic powder by using a combination of the aforementioned (A) carboxylic acid-modified silicone. When the (B) vinyl-based polymer emulsion is used alone, the effect of boosting the SPF value of the cosmetic composition is limited, and the effect of boosting the SPF value of the cosmetic composition by combining the two is sufficiently exhibited.

The vinyl-based polymer is a polymer or copolymer formed by polymerizing one or two or more types of vinyl-based monomers (monomers) having at least one vinyl copolymerizable functional group, and some of the monomers in the present invention may have a carbosiloxane dendrimer structure.

The vinyl-based polymer emulsion is obtained by preparing an emulsified dispersion in an aqueous medium containing a surfactant by adding a radical polymerization initiator to one type or two or more types of the vinyl-based monomers described above, and performing emulsion polymerization (polymerization reaction or copolymerization reaction). In this emulsion, the vinyl-based polymer is dispersed in the aqueous phase in the form of emulsion particles or latex particles, and the vinyl-based polymer is obtained as a solid by removing water by a drying method or the like.

Specific examples of the vinyl-based monomer include: lower alkyl (meth)acrylates such as methyl (meth)acrylate, ethyl (meth)acrylate, n-propyl (meth)acrylate, and isopropyl (meth)acrylate; glycidyl (meth)acrylate; higher (meth)acrylates such as n-butyl (meth)acrylate, isobutyl (meth)acrylate, tert-butyl (meth)acrylate, n-hexyl (meth)acrylate, cyclohexyl (meth)acrylate, 2-ethylhexyl (meth)acrylate, octyl (meth)acrylate, lauryl (meth)acrylate, and stearyl (meth)acrylate; lower fatty acid vinyl esters such as vinyl acetate and vinyl propionate; higher fatty acid esters such as vinyl butyrate, vinyl caproate, vinyl 2-ethylhexanoate, vinyl laurate, and vinyl stearate; aromatic vinyl-based monomers such as styrene, vinyl toluene, benzyl (meth)acrylate, phenoxyethyl (meth)acrylate, and vinyl pyrrolidone; amide group-containing vinyl-based monomers such as (meth)acrylamide, N-methylol (meth)acrylamide, N-methoxymethyl (meth)acrylamide, isobutoxymethoxy (meth)acrylamide, and N,N-dimethyl (meth)acrylamide; hydroxy group-containing vinyl-type monomers such as 2-hydroxyethyl (meth)acrylate, 2-hydroxybutyl (meth)acrylate, and 2-hydroxypropyl (meth)acrylate: fluorine-containing vinyl-type monomers such as trifluoropropyl (meth)acrylate, perfluorobutylethyl (meth)acrylate, and perfluorooctylethyl (meth)acrylate; epoxy group-containing vinyl-type monomers such as glycidyl (meth)acrylate and 3,4 epoxycyclohexylmethyl (meth)acrylate; carboxylic acid-containing vinyl-type monomers such as (meth)acrylic acid, itaconic acid, crotonic acid, fumaric acid, and maleic acid; ether bond-containing vinyl-based monomers such as tetrahydrofurfuryl (meth)acrylate, butoxyethyl (meth)acrylate, ethoxydiethylene glycol (meth)acrylate, polyethylene glycol (meth)acrylate, polypropylene glycol mono(meth)acrylate, hydroxybutyl vinyl ether, cetyl vinyl ether, and 2-ethylhexyl vinyl ether; unsaturated group-containing silicone compounds such as (meth)acryloxypropyl trimethoxysilane, (branched or linear) polydimethyl siloxane containing a (meth)acrylic group at one terminal, and a polydimethyl siloxane containing a styryl group at one terminal; butadiene; vinyl chloride; vinylidene chloride; (meth)acrylonitrile; dibutyl fumarate; maleic anhydride; dodecyl succinic anhydride; (meth)acrylic glycidyl ether; alkali metal salts, ammonium salts, organic amine salts of radically polymerizable unsaturated carboxylic acids such as (meth)acrylic acid, itaconic acid, crotonic acid, fumaric acid, and maleic acid; radical polymerizable unsaturated monomers having sulfonic acid groups such as styrene sulfonic acid, and their alkali metal salts, ammonium salts, organic amine salts; quaternary ammonium salts derived from (meth)acrylic acids, such as 2-hydroxy-3-methacryloxypropyl trimethylammonium chloride, methacrylates of alcohols with tertiary amine groups, such as diethylamine methacrylates, and quaternary ammonium salts thereof.

A polyfunctional vinyl-based monomer can also be used, and examples thereof include trimethylolpropane tri(meth)acrylate, pentaerythritol tri(meth)acrylate, ethylene glycol di(meth)acrylate, tetraethylene glycol di(meth)acrylate, polyethylene glycol di(meth)acrylate, 1,4-butanediol di(meth)acrylate, 1,6-hexanediol di(meth)acrylate, neopentyl glycol di(meth)acrylate, trimethylolpropane trioxyethyl (meth)acrylate, tris(2-hydroxyethyl)isocyanurate di(meth)acrylate, tris(2-hydroxyethyl)isocyanurate tri(meth)acrylate, (meth)acryloyl group-containing monomers such as di(meth)acrylate of diol, ethylene oxide of bisphenol A or adduct of propylene oxide, di(meth)acrylate of diol, ethylene oxide of hydrogenated bisphenol A or adduct of propylene oxide, and triethylene glycol divinyl ether, and unsaturated group-containing silicone compounds such as both-terminal styryl group-blocking polydimethylsiloxane and both-terminal methacryloxypropyl-blocking polydimethylsiloxane.

In addition to these, an organosilicon compound having a vinyl-based radical polymerizable unsaturated group and a hydrolyzable group can also be used. In this case, the film strength becomes hard and water repellency durability is improved, which is preferable. Here, examples of the radically polymerizable group include a (meth)acryloxy group-containing organic group, a (meth)acrylamide group-containing organic group, and a styryl group-containing organic group, as represented by the following general formulas, or an alkenyl group having from 2 to 10 carbon atoms, and a vinyloxy group and an allyloxy group.

The vinyl-based monomer may have a carbosiloxane dendrimer structure, and examples thereof include an acrylic acid ester monomer or a methacrylic acid ester monomer having a carbosiloxane dendrimer structure. Specific examples thereof are the same as Patent Document 4 (PCT International Publication No. WO 2017/061090). Furthermore, the polymerization of the carbosiloxane dendrimers can be produced according to the producing method disclosed in Japanese Unexamined Patent Application Publication No. H11-1530, Japanese Unexamined Patent Application Publication No. 2000-63225, Japanese Unexamined Patent Application Publication No. 2001-192424, Japanese Unexamined Patent Application Publication No. 2014-40512, and the like.

The radical polymerization initiator used in the synthesis of the vinyl polymer is not particularly limited as long as it is a radical polymerization initiator generally used in emulsion polymerization of a vinyl polymer. Examples thereof include water-soluble peroxides such as inorganic peroxides such as potassium persulfate, sodium persulfate, ammonium persulfate, and the like; and organic peroxides such as t-butylperoxymaleic acid, succinic acid peroxide, and t-butylhydroperoxide. If an oil-soluble radical initiator is used, it may be pre-emulsified and then mixed with other ingredients.

The emulsified dispersion is prepared using a general emulsification device. The polymerization temperature and reaction time can be appropriately determined according to the degree of polymerization of the desired vinyl polymer, the type of monomer, the final solid content concentration, and the like. Furthermore, the emulsified dispersion may be polymerized dropwise, or the emulsified dispersion may be charged in a batch and then polymerized, and the manufacturing step thereof is not particularly limited.

The vinyl polymer emulsion of the present invention may be in the form of an emulsion in which emulsified particles of a uniform vinyl polymer or vinyl copolymer are dispersed in an aqueous phase, and may be in the form of an emulsion in which latex particles of a vinyl copolymer having a core-shell structure are emulsified and dispersed in an aqueous phase.

As the (B) vinyl polymer emulsion in the present invention, an emulsion of an acrylic copolymer polymer obtained by copolymerizing an acrylate ester monomer or a methacrylate monomer is suitable, and the acrylic copolymer polymer may contain a functional group selected from alkyl groups having 6 or more carbon atoms, styrene groups, and carbosiloxane dendron structures, in which a portion of the hydrocarbon group may be substituted with fluorine or chlorine atoms. Furthermore, the polymer may be an acrylic copolymer polymer containing a hydrophilic group such as a hydroxyl group in the molecule.

Examples of the (B) vinyl polymer emulsion of the present invention include emulsions of one or more types of acrylic copolymer polymers selected from b1) an acrylic acid/alkyl methacrylate copolymer polymer;
(b2) an acrylic acid/styrene methacrylate copolymer polymer; and
(b3) an acrylic acid/methacrylic acid copolymer polymer having a carbosiloxane dendron structure.

Such component (B) can be synthesized by the above methods, but is commercially available, for example DOWNSIL™ FA-4103 ACRYLATE EMULSION sold by Dow Chemical/Dow Silicone; SOLTEX™ INO POLYMER; EPITEX™ 66 POLYMER; and LUVIFLEX® SOFT sold by SunSpheres, BASF.

In the oil-in-water emulsion cosmetic composition of the present invention, the compounding amount of the (B) vinyl polymer emulsion is not particularly limited, and as the solid content of the vinyl polymer excluding moisture from the emulsion (hereinafter, referred to as "solid content in emulsion"), it is preferably contained in a range of 0.1% to 10% by mass, more preferably in a range of 0.2% to 7.5% by mass, and still more preferably in a range of 0.5% to 5.0% by mass, based on the total mass of the cosmetic composition.

In the oil-in-water emulsion cosmetic composition of the present invention, in order to boost the SPF value of the cosmetic composition, the (B) vinyl polymer emulsion is preferably contained in an amount in the range of 0.5 to 10 parts by mass, and particularly preferably in an amount in the range in which the solid content in the emulsion is in the range of 1.0 to 7.5 parts by mass, with respect to 100 parts by mass of the (D) inorganic UV protecting agent consisting of hydrophobic fine particulate metal oxide described later. In the range described above, the component (D) is stably dispersed in the aqueous phase by the combination of the components (A) and the (B) vinyl polymer emulsion, and the effect of improving the SPF value of the whole cosmetic composition is excellent.

[(C) Basic Compound]

The oil-in-water emulsion cosmetic composition of the present invention contains at least one (C) basic compound. The component (C) is capable of anionizing the carboxylic acid modified moiety of the aforementioned (A) carboxylic acid-modified silicone, and improves the function of the (A) carboxylic acid-modified silicone as a surfactant. In particular, the oil-in-water emulsion cosmetic composition of the present invention contains the (D) inorganic UV protecting agent consisting of hydrophobic fine particulate metal oxide, but by using the component (A) and the component (C) in combination, as compared to the component (A) used alone, the component (D) can be satisfactorily dispersed in the aqueous phase of the oil-in-water emulsion cosmetic composition of the present invention, which not only improves the stability and film-forming property of the whole cosmetic composition, but also contributes to the effect of boosting the SPF value of the whole cosmetic composition as an auxiliary agent of the component (A).

The basic compound used in the present invention is not particularly limited as long as the basic compound is a compound that exhibits basicity when dissolved in water, and various types of inorganic compounds and organic compounds can be used. One or more types of basic compounds may be compounded.

Examples of the organic compound include monoethanolamine, triethanolamine, 2-amino-2-methyl-1,3-propanediol, aminomethyl propanol, 2-amino-2-hydroxymethyl-1,3-propanediol, arginine, guanidine, and the like.

Examples of the inorganic compounds include sodium hydroxide, sodium carbonate, potassium hydroxide, potassium carbonate, calcium hydroxide, calcium carbonate, ammonia, and the like. Among these, potassium hydroxide can be particularly suitably used.

The compounding amount of the basic compound in the oil-in-water emulsion cosmetic composition of the present invention is not particularly limited, but in a case of a monovalent base per 1 mol of carboxylic acid group contained in the carboxylic acid-modified silicone to be compounded, the carboxylic acid group/monovalent base (molar ratio) is preferably 1/0.5 to 1/1.5.

The pH of the oil-in-water emulsion cosmetic composition of the present invention may be acidic or alkaline, however, the carboxylic acid modified moiety of the aforementioned (A) carboxylic acid-modified silicone is anionized, and it is preferably weakly alkaline, in particular it is preferably in the range of 7.1 to 9.5, and more preferably in the range of 7.2 to 8.5, from the perspective of improving dispersibility with respect to the hydrophobic powder containing the component (D).

[(D) Inorganic UV Protecting Agent Consisting of Hydrophobic Fine Particulate Metal Oxide]

The oil-in-water emulsion cosmetic composition of the present invention contains an inorganic UV protecting agent, and the effect of blocking UV-B waves (wavelength 280 to 315 nm) derived from the components is further improved by using the aforementioned component (A) and component (B) in combination. The SPF value of an UV shielding effect is the aforementioned SPF value, but when the oil-in-water emulsion cosmetic composition of the present invention contains the same amount of the inorganic UV protecting agent, the SPF value of the whole cosmetic composition is improved and the effect of shielding ultraviolet light is further improved compared to a case where the component (A) and the component (B) are not contained. Furthermore, when the component (D) is the hydrophobic powder and is compounded in large quantities for the purpose of improving SPF value, the feeling of use of the oil-in-water emulsion cosmetic composition may be diminished, however, in the oil-in-water emulsion cosmetic composition of the present invention as described above, since the effect of boosting the SPF value of the whole cosmetic composition is stated, there is an advantage in that a high SPF value can be achieved with an amount of the component (D) used that does not impair the feeling of use. Furthermore, the component (D) of the present invention can be dispersed in the aqueous phase and the oil phase; however, by using the aforementioned basic compound (C), the oil-in-water emulsion cosmetic composition is well dispersed in the aqueous phase, and the feeling of use as a cosmetic composition, the UV protection effect, and the detergency with soap or the like are further improved.

The component (D) of the present invention is a hydrophobized metal oxide, which is an inorganic UV protecting agent having an ultraviolet light shielding effect. Examples of such a component (D) include one or two or more types of inorganic UV protecting agents selected from hydrophobic fine particulate titanium oxide and hydrophobic fine particulate zinc oxide. Here, the particle size of the hydrophobic fine particulate titanium oxide and hydrophobic fine particulate zinc oxide is preferably 1 to 200 nm in terms of ultraviolet protection effect and dispersibility, and more preferably 10 to 80 nm.

The hydrophobizing treatment in the component (D) is not particularly limited, and means that the powder is treated with various hydrophobized surface treatment agents. Examples of the hydrophobizing treatment include a methyl hydrogen polysiloxane (methylcone in Japanese cosmetics label name) treatment, a (dimethicone/methicone) copolymer (hydrogen dimethicone in Japanese cosmetics label) treatment, a dimethylpolysiloxane (dimethicone in Japanese cosmetics label) treatment, a carboxylic acid-modified silicone treatment, a silicone resin treatment, a silicone gum treatment, an acrylic silicone treatment, an organosiloxane treatment such as a fluorinated silicone treatment; a metal soap treatment such as a zinc stearate treatment, a silane coupling agent treatment; a silane treatment such as an alkylsilane treatment, a fluorine compound treatment such as a perfluoroalkyl phosphate ester salt; a perfluoro-ether treatment; an amino acid treatment such as an N-lauroyl-L-lysine treatment; an oil agent treatment such as a squalane treatment; and an acrylic acid treatment such as an alkyl acrylate treatment, and the like, and two or more of these treatments can be also used in combination.

Among these treatments, the treatment with the silicone compound is preferable from the perspective of the water resistance and ease of dispersion by the carboxylic acid-modified silicone. Among them, it is particularly preferable that the treatment is performed with methylhydrogenpolysiloxane, (dimethicone/methicone) copolymer, dimethylpolysiloxane, or alkylsilane.

The compounding amount of the component (D) in the oil-in-water emulsion cosmetic composition of the present invention is not particularly limited, however, is preferably from 1% to 40% by mass, more preferably from 2% to 35% by mass, and still more preferably from 5% to 20% by mass, based on the total mass of the cosmetic composition. As described above, the larger the compounding amount of the component (D) is, the higher the SPF value of the cosmetic composition is generally, but the feeling of use peculiar to the oil-in-water emulsion cosmetic composition tends to be impaired, and in the oil-in-water emulsion cosmetic composition of the present invention, by using the components (A) and (B), the SPF value of the whole cosmetic composition is boosted, and it is possible to design the cosmetic composition with a high SPF value without significantly impairing the feeling of use peculiar to the oil-in-water emulsion cosmetic composition. Note that a suitable compounding amount of the component (A) and the component (B) is as described above based on 100 parts by mass of the component (D).

[Other Hydrophobic Powders]

The oil-in-water emulsion cosmetic composition of the present invention may optionally contain a hydrophobic powder other than the component (D). These powders include white and colored pigments, body pigments. The white and colored pigments are used for coloring cosmetic compositions and the like, while extender pigments are used for improving the tactile sensation of the cosmetic compositions. In addition, when the surface of these powders itself is not hydrophobic, the surface thereof is subjected to a hydrophobization treatment in the same manner as the component (D) described above. Note that these hydrophobic powders may be complexed together.

The shape of the powder (spherical shape, rod shape, needle shape, plate shape, irregular shape, spindle shape, and the like), particle size (aerosol, fine particles, pigment grade, and the like), and particle structure (porous, non-porous, and the like) are not limited, and the average primary particle size is preferably in the range of 1 nm to 100 μm.

Examples of the hydrophobic powder other than the component (D) include inorganic powders, organic powders, surfactant metal salt powders (metal soaps), colored pigments, pearl pigments, metal powder pigments, and composites of these can also be used. Specifically, inorganic powders include zirconium oxide, cerium oxide, magnesium oxide, barium sulfate, calcium sulfate, magnesium sulfate, calcium sulfate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, magnesium aluminum silicate, calcium silicate, barium silicate, strontium silicate, metal tungstate, hydroxyapatite, vermiculite, hydrargilite, bentonite, montmorillonite, hectorite, zeolite, ceramic powder, dicalcium phosphate, alumina, aluminum hydroxide, boron nitride, boron nitride, and the like; organic powders include polyamide powder, polyester powder, polyethylene powder, and polypropylene powder, polystyrene powder, polyurethane powder, polystyrene powder, benzoganamine powder, polymethylbenzoganamine powder, polytetrafluoroethylene powder, polymethyl methacrylate powder, cellulose, silk powder, nylon powder, 12-nylon, 6-nylon, silicone powder, polymethylsilsesquioxane spherical powder, a styrene/acrylic acid copolymer, a divinylbenzene/styrene copolymer, a vinyl resin, a urea resins, a phenol resin, a fluororesin, a silicon resin, an acrylic resin, a melamine resin, an epoxy resin, a polycarbonate resin, microcrystalline fiber powder, starch powder, lauroyl lysine, and the like; surfactant metal salt powders include zinc stearate, aluminum stearate, calcium stearate, magnesium stearate, zinc myristate, magnesium myristate, zinc palmitate, zinc laurate, zinc cetyl phosphate, calcium cetyl phosphate, sodium zinc cetyl phosphate, and the like; colored pigments include inorganic red pigments such as red oxide, iron oxide, iron hydroxide, iron titanate, inorganic brown pigments such as γ-iron oxide, inorganic yellow pigments such as yellow iron oxide, black iron oxide, inorganic black pigments such as carbon black, inorganic purple pigments such as manganese violet, cobalt violet, and the like, inorganic green pigments such as chromium hydroxide, chromium oxide, cobalt oxide, cobalt titanate, and the like, inorganic blue pigments such as prussian blue, ultramarine blue, and the like; those obtained by laking tar dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, or those obtained by laking natural dyes such as carmine acid, lacquemic acid, carthamine, braziline, chrosine and the like; pearl pigments such as titanium oxide-coated mica, titanated mica, iron oxide-treated titanated mica, titanium oxide-coated mica, bismuth oxychloride, titanium oxide-coated bismuth oxychloride, titanium oxide-coated talc, fish scale foil, titanium oxide-coated colored mica and the like; oxidized titanium oxide coated mica, oxychlorinated bismuth, titanium oxide coated bismuth oxychloride, titanium oxide coated tantalum foil, fish scaly foil, titanium oxide coated colored mica, and the like; metal powder pigments such as aluminum, gold, silver, copper, platinum, stainless steel, and the like.

A silicone elastomer powder may also be used as the hydrophobic powder. The silicone elastomer powder is a crosslinked product of a liner diorganopolysiloxane mainly composed of a diorganosiloxy unit (D unit), and can be suitably obtained by crosslinking an organohydrogenpolysiloxane having a silicon-bonded hydrogen atom at the side chain or end and a diorganopolysiloxane having an unsaturated hydrocarbon group such as an alkenyl group at the side chain or end under a hydrosilylation reaction catalyst. Since the silicone elastomer powder is soft, elastic, and excellent in oil absorption compared to the silicone resin powder composed of a T unit and a Q unit, the silicone elastomer powder can absorb oil and fat on the skin and prevent cosmetic collapse.

The silicone elastomer powder may have various shapes, such as spherical, flat, or amorphous. The silicone elastomer powder may be in the form of an oil dispersion. The cosmetic composition of the present invention is a silicone elastomer powder having a particle shape, a primary particle diameter thereof determined by observation using an electron microscope and/or an average primary particle diameter measured by laser diffraction/scattering method falls within a range of 0.1 to 50 μm, and a silicone elastomer powder having a spherical primary particle shape can be suitably compounded. The silicone elastomer constituting the silicone elastomer powder is preferably a silicone elastomer having a hardness of 80 or less, more preferably 65 or less according to JIS K 6253 "Hardness testing method for rubber, vulcanized or thermoplastic" as measured by type-A durometer. In addition, these silicone elastomer powders may optionally be subjected to a surface treatment with a silicone resin, silica, or the like.

The compounding amount of the hydrophobic powder other than the component (D) is not particularly limited, but the total amount of the component (D) and the hydrophobic powder is preferably from 1% to 40% by mass, more preferably from 2% to 35% by mass, and still more preferably from 5% to 20% by mass, based on the total mass of the cosmetic composition.

The component (D) and the hydrophobic powder other than the component (D) are dispersible in the oil phase and/or in the aqueous phase, but in the present invention, the basic compound (C) is used, and these hydrophobic powder components are well dispersed in the aqueous phase. Furthermore, when the (G) polyhydric alcohol described below is used, these hydrophobic powders can be uniformly dispersed in the aqueous phase.

[(E) Oil Agent]

The cosmetic composition of the present invention includes at least one type of oil agent (E). The oil agent forms an oil phase in the cosmetic composition of the present invention.

The "oil agent" in the present invention is generally used as a component of a cosmetic composition, and is not particularly limited. The oil agent is usually liquid at room temperature, but may be a solid such as wax, or may be in the form of a highly viscous and viscous gum or paste, which will be described later.

The oil agent is preferably at least one type of liquid at 5° C. to 100° C. selected from the group consisting of silicone oil, a nonpolar organic compound, and a low polarity organic compound.

Silicone oils are hydrophobic, and their molecular structure may be cyclic, linear, or branched. The viscosities of silicone oils at 25° C. are usually in the range of 0.65 to 100,000 mm$^2$/s, preferably in the range of 0.65 to 10,000 mm$^2$/s.

Silicone oils include, for example, linear organopolysiloxanes, cyclic organopolysiloxanes, and branched organopolysiloxanes. Among these, linear organopolysiloxanes, cyclic organopolysiloxanes, and branched organopolysiloxanes that are volatile are preferable.

More specifically, examples of linear organopolysiloxanes include dimethylpolysiloxane capped at both molecular chain ends with trimethylsiloxy groups (dimethylsilicone having low viscosity such as 2 mPas or 6 mPas to high viscosity of 1,000,000 mPas), organohydrogenpolysiloxane, methylphenylpolysiloxane capped at both molecular chain ends with trimethylsiloxy groups, dimethylsiloxane/methylphenylsiloxane copolymer capped at both molecular chain ends with trimethylsiloxy groups, diphenylpolysiloxane capped at both molecular chain ends with trimethylsiloxy groups, dimethylsiloxane/diphenylsiloxane copolymer capped at both molecular chain ends with trimethylsiloxy groups, trimethylpentaphenyl trisiloxane, phenyl (trimethylsiloxy) siloxane, methyl alkyl polysiloxane capped at both molecular chain ends with trimethylsiloxy groups, dimethylpolysiloxane/methylalkylsiloxane copolymer capped at both molecular chain ends with trimethylsiloxy groups, dimethylsiloxane/methyl (3,3,3-trifluoropropyl) siloxane capped at both molecular chain ends with trimethylsiloxy groups, α,ω-dihydroxypolydimethylsiloxane, α,ω-diethoxypolymethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyl-trisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, higher alkoxy modified silicones, higher fatty acid modified silicones, dimethiconol and the like.

Examples of cyclic organopolysiloxanes include hexamethylcyclotrisiloxane (D3), octamethylcyclotetrasiloxane (D4), decamethylcyclopentasiloxane (D5), dodecamethylcyclotetrasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetra- methylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl) trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, 1,3,5,7-tetra(N, N-bis(lauroyl)-3-aminopropyl) tetramethylcyclotetrasiloxane, and the like.

Examples of the branched organopolysiloxane include methyltristrimethylsiloxysilane, ethyltristrimethylsiloxysilane, propyltristrimethylsiloxysilane, tetrakistrimethylsiloxysilane, and phenyltristrimethylsiloxysilane.

As the nonpolar organic compound and the low polarity organic compound, a hydrocarbon oil and a fatty acid ester oil are preferable. These are components which are widely used, in particular, as substrates for make-up cosmetics.

Examples of the hydrocarbon oil include liquid paraffin, light liquid isoparaffin, heavy liquid isoparaffin, petrolatum, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene polypropylene wax, scralan, squalene, pristane, polyisoprene, and the like.

Examples of the fatty acid ester oil include hexyldecyl octanate, cetyl octanate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, propylene glycol dioylate, glyceryl tri2-ethylhexanoate, tri2-ethylhexanoic acid trimethylolpropane, triethylhexanoic acid trimethylolpropane, (isostearic acid/sebacic acid) trimethylolpropane, trimethylolpropane trioctanoate, trimethylolpropane triisostearate, diisopropyl adipate, diisobutyl adipate, 2-hexyldecyl adipic acid, di-2-heptylundesyl adipate, diisostearyl malate, hydrogenated castor oil monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentyl glycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyl octyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearyl acid, dipentaerythritol fatty acid ester, 2-hexyldecyl myristate, ethyl laurate, N-lauroyl-L-glutamic acid-2-octyldodecyl ester, N-lauroyl-L-glutamic acid di(cholesteryl/behenyl/octyldodecyl), N-lauroyl-L-glutamic acid di (cholesteryl/octyldodecyl), N-lauroyl-L-glutamic acid di (phytosteryl/behenyl/octyldodecyl), N-lauroyl-L-glutamic acid di (phytosteryl/octyldodecyl), N-lauroyl L-glutamic acid di (phytosteryl/octyldodecyl), N-lauroyl sarcosine isopropyl, diisostearyl malate, neopentyl glycol dioctanoate, isodecyl neopentane, isotridecyl neopentane, isostearyl neopentane, isononyl isononanoate, isotridecyl isononanoate, octyl isononanoate, isotridecyl isononanoate, diethylpentanediol dineopenate, methylpentanediol dineopenate, octyldodecyl neodecanoate, 2-butyl-2-ethyl-1,3-propanediol dioctanoate, pentaerythrityl tetraoctanoate, hydrogenated rosin pentaerythrityl, pentaerythrityl triethylhexanoate, (hydroxystearic acid/stearic acid/logonic acid) dipentaerythrityl, polyglyceryl tetraisostearate, polyglyceryl nonaisostearate-10, deca (erucic acid/isostearic acid/ricinoleic acid) polyglyceryl-8, (hexyldecanoic acid/sebacic acid) diglyceryl oligoester, glycol distearate (ethylene glycol distearate), diisopropyl dimergelinoleate, diisostearyl dimersylinoleate, diisostearyl dimersylylate (isostearyl/phytosteryl), dimer dilinoleic acid (phytosteryl/behenyl), dimer dilinoleic acid (phytosteryl/isostearyl/cetyl/stearyl/behenyl), dimer dilinoleic acid dimer dilinoleyl, diisostearate dimer dilinoleil, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristinate, glyceryl triisopalmitate, glyceryl trioctanoate, glyceryl trioleate, glyceryl diisostearate, tri(caprylic acid/capric acid) glyceryl, tri (caprylic acid/capric acid/myristic acid/stearic acid) glyceryl, hydrogenated rosin triglyceride (hydrogenated ester gum), rosin triglyceride (ester gum), glyceryl becosanate, di-2-heptyl glyceryl undecanoate, diglyceryl myristate isostearate, cholesteryl acetate, cholesteryl nonanoate, cholesteryl stearate, cholesteryl isostearate, cholesteryl oleate, cholesteryl 12-hydroxystearate, macadamia nut oil fatty acid cholesteryl, macademia nut oil fatty acid phytosteryl, phytosteryl isostearate, soft lanolin fatty acid cholesteryl, hard lanolin fatty acid cholesteryl, long-chain branched fatty acid cholesteryl, long-chain a-hydroxy fatty acid cholesteryl, octyldodecyl ricinoleate, octyldodecyl lanolin fatty acid, octyldodecyl erucate, isostearic acid-hardened castor oil, avocado oil fatty acid ethyl, lanolin fatty acid isopropyl, and the like.

For example, higher alcohols having 10 to 30 carbon atoms can be used as the low polarity organic compound. When a higher alcohol is used as the emulsion stabilizing component, the amount of hydrophilic surfactant can be reduced, and the water resistance can be further improved. The higher alcohol is a saturated or unsaturated monohydric aliphatic alcohol, and the hydrocarbon group portion may be either linear or branched, but is more preferably linear. Examples of higher alcohols having 10 to 30 carbon atoms include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, lanolin alcohol, hydrogenated lanolin alcohol, and the like. In the present invention, it is preferable to use a higher alcohol having a melting point of from 40 to 80° C. alone, or to combine a plurality of higher alcohols so that the melting point is from 40 to 70° C.

The compounding amount of the oil agent in the cosmetic composition of the present invention is not particularly limited, and preferably from 3% to 60% by mass, more preferably from 4% to 50% by mass, still more preferably from 5% to 40% by mass, even more preferably 6% to 30% by mass, and even still more preferably 7% to 20% by mass, based on the total mass of the cosmetic composition.

(UV Absorber)

The (E) oil agent can include at least one type of UV absorber. That is, the oil phase of the cosmetic composition of the present invention can include a UV absorber. The UV absorber is preferably organic, more preferably lipophilic, and even more preferably oil soluble. In addition to the inorganic UV protecting component that is the component (D) described above, by including an organic UV absorber that is an (E) oil agent, a higher SPF value can be achieved as the whole cosmetic composition, and the ultraviolet light blocking/shielding effect can be further improved with respect to UV-A waves (wavelength: 315 to 380 nm) other than UV-B waves (wavelength 280 to 315 nm). Note that the oil-in-water emulsion cosmetic composition according to the present invention preferably can include a (H) water-soluble UV absorber described below, in addition to the UV absorber that is the (E) oil agent.

The oil-soluble UV absorber is not particularly limited as long as it is used in cosmetic compositions or skin external use preparations, and examples thereof include those described below. The oil-soluble UV absorber can be used alone or as a mixture of two or more types.

cinnamic acid-based UV absorbers such as benzyl paramethoxycinnamate, 2-ethylhexyl paramethoxycinnamate, and mono-2-ethylhexanoate glyceryl diparamethoxycinnamate; benzophenone-based UV absorbers such as hydroxymethoxybenzophenone, dihydroxymethoxybenzophenone, dihydroxybenzophenone, and tetrahydroxybenzophenone;

benzoic acid ester-based UV absorbers such as para-aminobenzoic acid, ethyl para-aminobenzoate, glyceryl para-aminobenzoate, amyl para-dimethylaminobenzoate, octyl para-dimethylaminobenzoate, 4-[N,N-di(2-hydroxypropyl) amino] ethyl benzoate, and diethylaminohydroxybenzoyl hexyl benzoate;

salicylic acid-based UV absorbers such as ethylene glycol salicylate, phenyl salicylate, octyl salicylate, benzyl salicylate, para-salicylate, and homomenthyl salicylate;

triazine-based UV absorbers such as ethylhexyltriazone (2,4, 6-tris[4-(2-ethylhexyloxycarbonyl) anilino] 1,3,5-triazine), and bisethylhexyloxyphenol methoxyphenyl triazine; and other UV absorbers such as 4-tert-butyl-4'-methoxydibenzoylmethane, menthyl anthranilate, 2-(2-hydroxy-5-methylphenyl) benzotriazole, 2-ethylhexyl dimethoxybenzidene dioxoimidazolidine propionate, octocrylene, and dimethicodiethyl benzalmalonate.

Among these, when selecting the UV absorbers such as 2-ethylhexyl paramethoxycinnamate, and mono-2-ethylhexanoate glyceryl diparamethoxycinnamate, octyl salicylate, homomenthyl salicylate, bisethylhexyloxyphenol methoxyphenyl triazine, dihydroxybenzophenone, octocrylene, 4-tert-butyl-4'-methoxydibenzoylmethane, diethylaminohydroxybenzoyl hexyl benzoate, and the like, a particularly high UV protection effect can be obtained.

The compounding amount of the UV absorber in the cosmetic composition of the present invention is not particularly limited, but is preferably from 3% to 30% by mass, more preferably from 5% to 25% by mass, and still more preferably from 7% to 20% by mass, based on the total mass of the cosmetic composition.

[Water]

The oil-in-water emulsion cosmetic composition of the present invention contains water. The water is a component that forms an aqueous phase in the cosmetic composition of the present invention, and in addition to the emulsified particles of the (E) oil agent described above, the water has a structure in which the component (D) and the other hydrophobic powder are stably dispersed in the aqueous phase in the presence of the component (A) and the component (C).

The compounding amount of the water in the cosmetic composition of the present invention is not particularly limited, but is preferably from 20% to 95% by mass, more preferably from 40% to 80% by mass, still more preferably from 45% to 70% by mass, even more preferably 47% to 65% by mass, and even still more preferably 50% to 60% by mass, based on the total mass of the cosmetic composition.

[(F) Oil-Soluble Film Forming Agent]

The oil-in-water emulsion cosmetic composition of the present invention may contain at least one (F) oil-soluble film forming agent. By using the component (A) to the component (D) described above, particularly the carboxylic acid-modified silicone that is the component (A), and the (F) oil-soluble film forming agent, the whole cosmetic composition can have a high stability and it is possible to provide an oil-in-water emulsion cosmetic composition that provides a cosmetic film with excellent water resistance.

The type of the (F) oil-soluble film forming agent is not particularly limited, and is preferably a silicone-based film-forming agent.

It is more preferably at least one selected from the group consisting of (F1) silicone resin containing an M unit and a Q unit, (F2) silicone acrylate, (F2) a silicone resin containing a T unit, and (F3) silicone gum.

A silicone resin containing (F1) silicone resin containing an M unit and a Q unit may be any silicone resin normally used in the cosmetic composition. As the (D1) silicone resin containing an M unit and a Q unit, any silicone resin can be used as long as it has a triorganosiroxy unit (M unit) (for example, an organo group is only an alkyl group such as a methyl group, or an alkyl group such as a methyl group and an allyl group such as a vinyl group or an aryl group such as a phenyl group) and a silicon unit (Q unit), and examples thereof include a MQ resin, a MDQ resin, and a MDTQ resin (D represents a diorganosyloxy unit, for example, an organo group is only an alkyl group such as a methyl group, or an alkyl group such as a methyl group and an allyl group such as a vinyl group or an aryl group such as a phenyl group). More specifically, trimethyl siloxysilicate, polyalkyl siloxysilicate, trimethyl siloxysilicate containing dimethylsiloxy units, and alkyl (perfluoroalkyl) siloxysilicate are exemplified. It is particularly preferable that these silicone resins are oil-soluble and can be dissolved in tetracyclosiloxane (D4) and pentacyclosiloxane (D5).

Among these, trimethyl siloxysilicate is preferable. Examples of commercially available products include 749 Fluid (available from Dow Toray Co., Ltd.) in which trimethyl siloxysilicate is previously dissolved in a solvent, X-21-5595, KF-7312J, and KF-7312F (all available from Shin-Etsu Chemical Co., Ltd.). These may be used alone, or may be used in combination as appropriate.

Examples of the (F2) silicone acrylate include copolymers having a polyalkyl acrylate backbone and a dimethicone polymer grafted onto the alkyl ester side chain, such as a copolymer of cyclopentasiloxane (and) acrylate/dimethicone (KP-545, available from Shin-Etsu Chemical Co., Ltd.) and a copolymer of methyl trimethicone (and) acrylate/dimethicone (KP-549, available from Shin-Etsu Chemical Co., Ltd.). Also, copolymers having a polyalkyl acrylate backbone and a siloxane dendron structure grafted onto the alkyl ester side chain, such as FA-4001CM SILICONE ACRYLATE, FA-4002ID SILICONE ACRYLATE, FA-4003DM SILICONE ACRYLATE, and FA-4004ID SILICONE ACRYLATE (available from Dow Toray Co., Ltd.), which is (acrylate/polytrimethylsiloxy methacrylate) copolymer, can be exemplified. These may be used alone, or may be used in combination as appropriate.

The (F3) silicone resin containing a T unit may be any silicone resin normally used in the cosmetic composition. As the (F3) silicone resin containing a T unit, any silicone resin can be used as long as it has a monoorganosiloxy unit (T unit) (for example, the organo group is an alkyl group such as a methyl group, or an allyl group such as a vinyl group or an aryl group such as a phenyl group), and examples thereof include a MTQ resin, a MDTQ resin, a TD resin, a TQ resin, a TDQ resin, and the like. It is particularly preferable that these silicone resins are oil-soluble and can be dissolved in D4 and D5.

Specific examples of the (F3) silicone resin containing a T unit include 670 Fluid, which is polypropylsilsesquioxane, SW-8005 C30 resin wax, which is an alkyl (C30-45) dimethylsilylpolypropylsilsesquioxane (available from Dow Toray Co., Ltd.), and the like. These may be used alone, or may be used in combination as appropriate.

Examples of the (F4) silicone resin include FC-5002IDD RESIN GUM (available from Dow Toray Co., Ltd.), which is a (trimethyl siloxysilicate/dimethiconol) crosspolymer, and the like.

The compounding amount of the oil-soluble film forming agent in the cosmetic composition of the present invention is from 0.01% to 5% by mass, preferably from 0.05% to 3% by mass, and more preferably from 0.10% to 2% by mass, based on the total mass of the cosmetic composition.

[(G) Polyhydric Alcohol]

The oil-in-water emulsion cosmetic composition of the present invention can contain at least one (G) polyhydric alcohol.

By containing polyhydric alcohols, the moisturizing feeling and the feeling of use of the cosmetic composition of the present invention can be adjusted, and when the cosmetic composition of the present invention contains the hydrophobic powder such as the component (D), the component (A) and hydrophobic powder are premixed with polyhydric alcohol and then mixed with other components to prepare the cosmetic composition, and thereby the hydrophobic powder can be well dispersed in the aqueous phase.

Examples of the polyhydric alcohols include sorbitol, xylitol, propylene glycol, dipropylene glycol, 1,3-butylene glycol, glycerin, diglycerin, polyethylene glycol, and the like, and these polyhydric alcohols can be used alone or in combination of two or more types. When the component (A) and the hydrophobic powder are pre-mixed together with the polyhydric alcohol, the liquid polyhydric alcohol can be uniformly dispersed in the aqueous phase. Among these, propylene glycol, dipropylene glycol, 1,3-butylene glycol, glycerin, diglycerin, and combinations thereof are preferable.

The compounding amount of the polyhydric alcohol in the cosmetic composition of the present invention is not particularly limited, and preferably from 0.3% to 30% by mass, more preferably from 0.5% to 25% by mass, still more preferably from 1% to 20% by mass, even more preferably 2% to 20% by mass, and even still more preferably 3% to 15% by mass, based on the total mass of the cosmetic composition.

[(H) Water-Soluble UV Absorber]

In addition to the oil phase, the oil-in-water emulsion cosmetic composition of the present invention may also contain a UV absorber for the aqueous phase, and may further improve the SPF value and a PA index value of the overall amount of makeup. Specifically, it may contain at least one (H) water-soluble UV absorber soluble in the aqueous phase.

The type and amount of such water-soluble UV absorber is not particularly limited as long as it is used in a cosmetic composition or a skin external use preparation, and examples thereof include phenyl benzimidazole sulfonic acid (PBSA), 2-hydroxy-4-methoxybenzophenone, telephthalilidene dicamphor sulfonic acid (Mexoryl (trademark) SX), oxybenzone-4, benzophenone-4, benzophenone-5, benzylidene camphorsulfonic acid, cinnamaldehyde-trimonium chloride, methoxycinnamide-propylethyldimonium chloride ether, disodium bisethylphenyl triaminotriazine stilbene disulfonate, disodium distyrylbiphenyl disulfonate, phenyldivene imidazole disodium tetrasulfonate, methoxycinnamide-propylhydroxysultaine, methoxycinnamide-propylrauldimonium tosylate, PEG-25 PABA (p-aminobenzoic acid), polyquaternium-59, TEA-Salicylate, and salts, derivatives, and mixtures thereof. Preferably, phenyl benzimidazole sulfonic acid, telephthalilidene dicamphor sulfonic acid, and salts thereof are exemplified. These may be used alone, or two or more types may be used in combination, but when compounding two or more types of UV absorbers that are the oil agents described above, it is desirable to select only one type of water-soluble UV absorber or reduce the amount of the UV absorber.

The compounding amount of the water-soluble UV absorber in the cosmetic composition of the present invention is not particularly limited, and is preferably from 0.1% to 30% by mass, more preferably from 0.2% to 25% by mass, still more preferably from 0.3% to 20% by mass, and even more preferably 0.3% to 15% by mass, based on the total mass of the cosmetic composition.

[Optional Components]

Other components generally used in cosmetic compositions can be added to the oil-in-water emulsion cosmetic composition of the present invention within a range that does not hinder the effect of the present invention, and examples of other such components include: hydrophilic powders, moisturizing agents other than component (G), thickeners other than component (B) (for example, water-soluble thickener such as methyl cellulose and guar gum), gelling agents, antiseptic agents, antimicrobial agents, perfumes, salts, antioxidants, pH adjusting agents other than component (C), chelating agents, refreshing agents, anti-inflammatory agents, physiologically active components (skin lightening agents, cell activating agents, rough skin improving agents, circulation promoters, skin astringents, anti-seborrheic agents, and the like), vitamins, amino acids, nucleic acids, hormones, and inclusion compounds. Other components are not particularly limited.

The oil-in-water emulsion cosmetic composition of the present invention may contain a salt of saturated or unsaturated fatty acid of at least one higher fatty acid, and specific examples thereof include lauric acid, myristic acid, palmitic acid, stearic acid, behenic acid, undecylenic acid, oleic acid, linoleic acid, linolenic acid, arachidonic acid, eicosapentaenoic acid (EPA), hexyldecanoic acid, docosahexaenoic acid (DHA), isostearic acid, and 12-hydroxystearic acid. The salt of such a higher fatty acid is a component that also functions as an emulsifier, but in the present invention, particularly preferably, the salt does not contain an emulsifier other than the component (A).

[Producing Method]

The manufacturing steps of the oil-in-water emulsion cosmetic composition of the present invention is optional and is not particularly limited as long as it is possible to prepare an oil-in-water emulsion cosmetic composition containing (A) carboxylic acid-modified silicone in a liquid form at 50° C., (B) a vinyl-based polymer emulsion, (C) a basic compound, (D) an inorganic UV protecting agent consisting of hydrophobic fine particulate metal oxide, and (E) an oil agent and water, by mixing the aforementioned components.

For example, the oil-in-water emulsion cosmetic composition of the present invention can be manufactured in such a manner that after the step of pre-mixing (D) an inorganic UV protecting agent consisting of hydrophobic fine particulate metal oxide, (E) an oil agent, (A) carboxylic acid-modified silicone, and optionally (G) polyhydric alcohol (such as a slurry composition as a precursor), a mixture obtained by the pre-mixing step is emulsified using a mechanical force in water, and further mixed with the (B) vinyl-based polymer emulsion, the (C) basic compound, and the residual water. In particular, it is preferable that the use of the (C) basic compound has a structure of an aqueous dispersion in which the hydrophobic powder is dispersed in the aqueous phase at pH 6.5 to 14.0. Note that, among the optional components described above, an oil-based material is preferably added in a pre-mixing step including the (E) oil agent, and an optional water-based material (for example, (H) water-soluble UV absorber) is preferably mixed in water in advance.

[How to Use]

The oil-in-water emulsion cosmetic composition of the present invention may be in the form of a cream, a gel, an emulsion, or a liquid, for example, the cosmetic composition of the present invention can be used as a base cosmetic composition such as emulsion, cream, serum, or the like, a base cosmetic composition, and a makeup cosmetic compositions such as sunscreen agent, foundation, eye shadow, eyeliner, and water powders, and the like, and can also be used as a sunscreen agent for hair and scalp, a temporary hair dye, and the like. Furthermore, the embodiments of the sunscreen cosmetic composition described below are not particularly limited, and can be used in the form of a lotion, liquid, gel, mist spray (including an aerosol type), liquid, solid, oil, foam, or the like.

The oil-in-water emulsion cosmetic composition of the present invention can also be used as a precursor for a cosmetic composition (premix or material for a cosmetic composition).

The oil-in-water emulsion cosmetic composition of the present invention is in the form of an oil-in-water emulsion composition, and since water constituting the continuous phase is in direct contact with the skin, it is possible to provide a much more fresh and refreshing feeling of use.

The oil-in-water emulsion cosmetic composition of the present invention is preferably a skin cosmetic composition, and is more preferably applied on weak acid skin, for example, and even more preferably is applied on skin having a pH of 5.1 to 7.0.

In addition, when the oil-in-water emulsion cosmetic composition of the present invention is applied onto the skin at an applied amount of 0.5 mg/cm$^2$, after 30 minutes, the pH of the applied surface is preferably 7.0 or less, and more preferably 6.7 or less.

The oil-in-water emulsion cosmetic composition of the present invention is stable and can form a cosmetic film having excellent water resistance on the skin, so that the makeup does not easily come off due to sweat, rain, and the like, and the makeup retention is excellent.

[Sunscreen Cosmetic Composition]

The oil-in-water emulsion cosmetic composition of the present invention has an improved SPF value, which is an index of the degree of effect of blocking UV-B waves (wavelength 280 to 315 nm) while taking advantage of the above tactile sensation and the like, and is particularly suitable for the sunscreen cosmetic composition. The sunscreen cosmetic composition which is the oil-in-water emulsion cosmetic composition of the present invention has a higher SPF value as the whole cosmetic composition than the SPF value achieved by the component (D) used alone when the sunscreen cosmetic composition does not contain a combination of the components (A) to (D).

The oil-in-water emulsion cosmetic composition of the present invention is based on the measurement of SPF of 2 mg per 1 cm$^2$ applied to the skin. The SPF value of the oil-in-water emulsion cosmetic composition of the present invention is preferably 5 or more, more preferably 25 or more, and is easily designed to have a high SPF value of 30 to 100. In particular, in the oil-in-water emulsion cosmetic composition of the present invention, a boost of an SPF value that is near 15% to 100% with respect to the SPF value realized by the component (D) alone can be expected. That is, it is possible to provide an oil-in-water emulsion cosmetic composition with an SPF value of 50 to 80 without impairing the tactile sensation as a cosmetic composition in a formulation in which a sunscreen cosmetic composition with an SPF value of about 40 is designed to maintain the tactile sensation peculiar to the oil-in-water emulsion cosmetic composition.

The oil-in-water emulsion cosmetic composition of the present invention can design a sunscreen cosmetic composition that is excellent in the PA index (abbreviation of Protection grade of UVA) as an index of the degree of effect of blocking UV-A waves (wavelength 315 to 380 nm) by selecting the component (D), the component (H), and other organic UV absorbers. Specifically, by using a diethylaminohydroxybenzoyl hexyl benzoate (registered trademark Uvinul A, BASF Japan), or the like, which is a UV absorber active in a UV-A region, in combination, it is possible to design sunscreen cosmetic compositions having a PA index of +(effective) or higher, and preferably PA++ or higher.

As described above, the oil-in-water emulsion cosmetic composition of the present invention has excellent stability and water resistance of a cosmetic film, and therefore, when used as a sunscreen cosmetic composition, in addition to a high UV protection effect, the makeup is less likely to come off due to sweat, rain, or the like, and the makeup retention is excellent. Furthermore, since the component (A) can be easily cleaned with an alkaline soap or the like, the present invention has the advantage of having excellent water resistance and makeup retention, and since the sunscreen cosmetic composition can be easily washed out with soap or the like, it also has the advantage that it is less likely to cause problems of skin irritation and sensitization during long-term use.

Hereinafter, the present invention is described in greater detail through examples; but the present invention is not limited thereto.

Example 1

Hereinafter, the present invention will be described in more detail based on examples, but the present invention is not limited to these examples. The compounding amount of each component is "% by mass" ("wt %") unless otherwise specified.

carboxylic acid-modified silicone (compound 1), which is a component (A) of the present invention, was synthesized by the following method.

Synthesis Example 1

In a flask equipped with a stirrer, a reflux condenser, a dropping funnel, and a thermometer, 230.67 g of trimethylsilyl undecylenate and 0.042 g of platinum-1,3-divinyl-1,1,3,3-tetramethyldisiloxane complex were added, and then 129.33 g of Si—H siloxane represented by the following general formula was added dropwise while keeping a temperature range of 70° C. to 80° C.

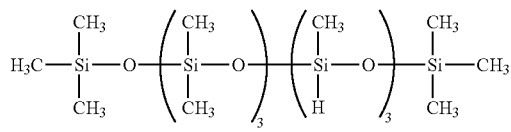

After dropping was complete, the mixture was aged for 2 hours at 110° C., and then the disappearance of the Si—H bond was confirmed by a hydrogen generation method. The low boiling point content was distilled off under reduced pressure. Thereafter, 90 g of deionized water was added, aged at reflux for 4 hours, and deprotection was performed. Thereafter, the low boiling point content was again removed under reduced pressure to obtain a compound 1. As a result of the analysis, it was confirmed that it was the compound 1 represented by the following chemical structural formula.

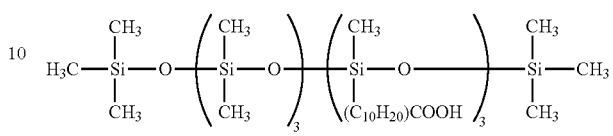

Examples 1 to 12 and Comparative Example 1

The compositions of Examples 1 to 12 and Comparative Example 1 were produced using the components shown in Table 1 to 3 by the producing method described below. The compounding amount of each component in Table 1 represent "% by mass" ("wt %") unless otherwise specified.

(Producing Method)
(1) Components of phase A are mixed.
(2) Components of phase B are mixed.
(3) Components of phase C are mixed.
(4) Emulsion is prepared by adding mixture of components of phase A to mixture of components of phase B in small amount at ambient temperature.
(4) Components of phase C are mixed into the emulsion.
(5) Cosmetic composition is prepared by mixing components of phase D into the emulsion.

TABLE 1

| | | | Comparative Example 1 | Comparative Example 2 | Comparative Example 3 |
|---|---|---|---|---|---|
| A | 1 | carboxylic acid-modified silicone (Note 1) | 1.5 | 1.5 | 1.5 |
| | 2 | Glycerin | 5 | 5 | 5 |
| | 3 | Sodium hydroxide solution 50% of aqueous solution | 0.5 | 0.5 | 0.5 |
| | 4 | Caprylic/capric triglyceride | 2 | 2 | 2 |
| | 5 | ethylhexyl methoxycinnamate | 7.5 | 7.5 | 7.5 |
| | 6 | Diethylaminohydroxybenzoyl hexyl benzoate | 2 | 2 | 2 |
| B | 6 | Acrylate copolymer 28% aqueous dispersion (Note 2) | 4 | 4 | 4 |
| | 7 | Purified water | Residue | Residue | Residue |
| | 8 | Triethanolamine | 0.47 | 0.47 | 0.47 |
| | 9 | Phenoxyethanol | 0.9 | 0.9 | 0.9 |
| C | 10 | Fine particulate titanium oxide (Note 3) | 7.98 | 7.98 | 7.98 |
| | 11 | 1,3-butylene glycol | 2.65 | 2.65 | 2.65 |
| | 12 | Purified water | 15.97 | 7.97 | 5.97 |
| D | 13 | (Acrylate/methacryloxyethyl phosphate) copolymer 31% aqueous dispersion (Note 4) | | 8 | |
| | 14 | (Styrene/acrylate) copolymer 25% water dispersion (Note 5) | | | 10 |
| | | Total | 100 | 100 | 100 |
| | | pH | 7.5 | 7.0 | 7.5 |
| | | Evaluation results | | | |
| | | Feeling of use (fresh) | ◎ | ◎ | ◎ |
| | | SPF value | 15.9 | 70.8 | 24.1 |
| | | PA value | ++ | +++ | ++ |

TABLE 2

|   |   |   | Example 1 | Example 2 | Example 3 | Example 4 | Example 5 |
|---|---|---|---|---|---|---|---|
| A | 1 | carboxylic acid-modified silicone (Note 1) | 1.5 | 1.5 | 1.5 | 1.5 | 1.5 |
|   | 2 | Glycerin | 5 | 5 | 5 | 5 | 5 |
|   | 3 | Sodium hydroxide solution 50% of aqueous solution | 0.5 | 0.5 | 0.5 | 0.5 | 0.5 |
|   | 4 | Caprylic/capric triglyceride | 2 | 2 | 2 | 2 | 2 |
|   | 5 | ethylhexyl methoxycinnamate | 7.5 | 7.5 | 7.5 | 7.5 | 7.5 |
|   | 6 | Diethylaminohydroxybenzoyl hexyl benzoate | 2 | 2 | 2 | 2 | 2 |
| B | 6 | Acrylate copolymer 28% aqueous dispersion (Note 2) | 4 | 4 | 4 | 4 | 4 |
|   | 7 | Purified water | Residue | Residue | Residue | Residue | Residue |
|   | 8 | Triethanolamine | 0.47 | 0.47 | 0.47 | 0.47 | 0.47 |
|   | 9 | Phenoxyethanol | 0.9 | 0.9 | 0.9 | 0.9 | 0.9 |
| C | 10 | carboxylic acid-modified silicone (Note 1) | 1.33 | 1.33 | 1.33 | 1.33 | 1.33 |
|   | 11 | Aminomethyl propanol | 0.38 | 0.38 | 0.38 | 0.38 | 0.38 |
|   | 12 | Fine particulate titanium oxide (Note 3) | 7.98 | 7.98 | 7.98 | 7.98 | 7.98 |
|   | 13 | 1,3-butylene glycol | 6.65 | 6.65 | 6.65 | 6.65 | 6.65 |
|   | 14 | Purified water | 10.64 | 10.64 | 10.64 | 10.64 | 10.64 |
| D | 15 | (Acrylate/methacryloxyethyl phosphate) copolymer 31% aqueous dispersion (Note 4) |  | 8 |  |  |  |
|   | 16 | (Styrene/acrylate) copolymer 25% water dispersion (Note 5) |  |  | 10 |  |  |
|   | 17 | (Acrylate/polytrimethylsiloxy methacrylate) copolymer 30% water dispersion (Note 6) |  |  |  | 4 |  |
|   | 18 | Acrylate copolymer 45% aqueous dispersion (Note 7) |  |  |  |  | 4 |
|   |   | Total | 100 | 100 | 100 | 100 | 100 |
|   |   | pH | 7.5 | 7.5 | 7.5 | 7.5 | 7.5 |
|   |   | Evaluation results |  |  |  |  |  |
|   |   | Feeling of use (fresh) | ◎ | ◎ | ◎ | ◎ | ◎ |
|   |   | SPF value | 47.8 | 83.2 | 62.3 | 54.8 | 68.6 |
|   |   | PA value | +++ | +++ | +++ | +++ | +++ |

TABLE 3

|   |   |   | Example 6 | Example 7 | Example 8 | Example 9 | Example 10 |
|---|---|---|---|---|---|---|---|
| A | 1 | carboxylic acid-modified silicone (Note 1) | 1.5 | 1.5 | 1.5 | 1.5 | 1.5 |
|   | 2 | Glycerin | 5 | 5 | 5 | 5 | 5 |
|   | 3 | Sodium hydroxide solution 50% of aqueous solution | 0.5 | 0.5 | 0.5 | 0.5 | 0.5 |
|   | 4 | Caprylic/capric triglyceride | 2 | 2 | 2 | 2 | 2 |
|   | 5 | ethylhexyl methoxycinnamate | 7.5 | 7.5 | 7.5 | 7.5 | 7.5 |
|   | 6 | Diethylaminohydroxybenzoyl hexyl benzoate | 2 | 2 | 2 | 2 | 2 |
| B | 6 | Acrylate copolymer 28% aqueous dispersion (Note 2) | 4 | 4 | 4 | 4 | 4 |
|   | 7 | Purified water | Residue | Residue | Residue | Residue | Residue |
|   | 8 | Triethanolamine | 0.47 | 0.47 | 0.47 | 0.47 | 0.47 |
|   | 9 | Phenoxyethanol | 0.9 | 0.9 | 0.9 | 0.9 | 0.9 |
| C | 10 | carboxylic acid-modified silicone (Note 1) | 1.33 | 1.33 | 1.33 | 1.33 | 1.33 |
|   | 11 | Aminomethyl propanol | 0.38 | 0.38 | 0.38 | 0.38 | 0.38 |
|   | 12 | Fine particulate titanium oxide (Note 3) | 7.98 | 7.98 | 7.98 | 7.98 | 7.98 |
|   | 13 | 1,3-butylene glycol | 6.65 | 6.65 | 6.65 | 6.65 | 6.65 |
|   | 14 | Purified water | 10.64 | 10.64 | 10.64 | 10.64 | 10.64 |
| D | 15 | (Acrylate/methacryloxyethyl phosphate) copolymer 31% aqueous dispersion (Note 4) | 4 | 4 |  |  |  |

TABLE 3-continued

|  | | Example 6 | Example 7 | Example 8 | Example 9 | Example 10 |
|---|---|---|---|---|---|---|
| 16 | (Styrene/acrylate) copolymer 25% water dispersion (Note 5) | | | 4 | 4 | 4 |
| 17 | (Acrylate/polytrimethylsiloxy methacrylate) copolymer 30% water dispersion (Note 6) | 10 | | 10 | 10 | |
| 18 | Acrylate copolymer 45% aqueous dispersion (Note 7) | 8 | 8 | 8 | | 8 |
|  | Total pH | 7.5 | 7.5 | 7.5 | 7.5 | 7.5 |
|  | Evaluation results | | | | | |
|  | Feeling of use (fresh) | ◎ | ◎ | ◎ | ◎ | ◎ |
|  | SPF value | 151 | 89.3 | 91.2 | 53.5 | 90.1 |
|  | PA value | +++ | +++ | +++ | +++ | +++ |

Note 1:
carboxylic acid-modified silicone of Synthesis Example 1
Note 2:
ACULYN ™ 33A RHEOLOGY MODIFIER (available from The Dow Chemical Company)
Note 3:
MTY-02 (available from Tayca Corporation)
Note 4:
SOLTEX ™ INO POLYMER (available from The Dow Chemical Company)
Note 5:
SunSpheres ™ PGL SPF Booster (available from The Dow Chemical Company)
Note 6:
DOWSIL ™ FA-4103 SILICONE ACRYLATE EMULSION (available from Dow Toray Co., Ltd.)
Note 7:
EPITEX ™ 66 POLYMER (available from The Dow Chemical Company)

For each oil-in-water emulsion cosmetic composition of Example 1 to 10 and Comparative Example 1 to 3, the feeling of use (freshness, refreshing feeling), SPF value, and PA value were evaluated according to the following evaluation methods. The results are shown in Table 1 to 3 together.

[Feeling of Use]

An evaluation target (sunscreen cosmetic composition) was applied to the faces of 20 female panelists, and the feeling of use (freshness, refreshing feeling) at the time of application was sensory evaluated according to the following criteria.

◎: 16 or more out of 20 responded fresh and refreshing
○: 11 to 15 out of 20 responded fresh and refreshing
Δ: 6 to 10 out of 20 responded fresh and refreshing
x: 5 or less out of 20 responded fresh and refreshing

[SPF Value and PA Value]

An evaluation target (sunscreen cosmetic composition) was uniformly applied to HELIOPLATE HD6 (available from HelioScreenLab) so as to be 2 mg/cm2 to measure the SPF value and PA value using the SPF measuring device UV-1000S (available from Labsphere). The values listed in Table 1 to 3 are average values excluding the maximum value and the minimum value by performing 10 measurement on each of three test samples.

From the evaluation results of Examples 1 to 10 and Comparative Examples 1 to 3, Examples 1 to 10 in which the vinyl-based polymer emulsion was included in the aqueous phase together with the carboxylic acid-modified silicone and the hydrophobic powder exhibited high SPF values and PA values without impairing the feeling of use. On the other hand, in Comparative Examples 1 to 3, which did not contain the vinyl-based polymerization emulsion, sufficient SPF value and PA value were not able to be obtained for the corresponding examples.

The invention claimed is:

1. An oil-in-water emulsion cosmetic composition comprising:
   (A) a carboxylic acid-modified silicone in a liquid form at 50° C.;
   (B) a vinyl-based polymer emulsion;
   (C) a basic compound; and
   (D) an inorganic UV protecting agent consisting of hydrophobic fine particulate metal oxide;
   wherein the (A) carboxylic acid-modified silicone is represented by the following structural formula (2):

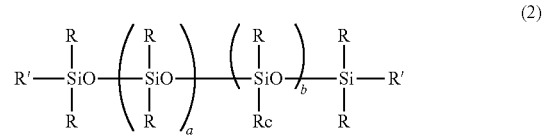

wherein:
   Rc represents a carboxyl group-containing organic group represented by a general formula:
   —R$^1$—(OR$^2$)p-(O)w-R$^3$—COOH, where R$^1$ represents a linear or branched alkylene group having 2 to 22 carbon atoms, R$^2$ represents a linear or branched alkylene group having 2 to 4 carbon atoms, R$^3$ represents a bond (-) or a linear or branched alkylene group having 1 to 22 carbon atoms, p represents a number from 0 to 200, and w represents a number of 0 or 1,
   R represents the same or different alkyl or alkoxy group having 1 to 22 carbon atoms, or a phenyl group,
   R' is Rc or R, and
   each of a and b is a positive number, (a+b) is a number in a range of 2 to 20, and a/b is in a range of 0.3 to 3.0.

2. The oil-in-water emulsion cosmetic composition according to claim 1, wherein for 100 parts by mass of the (D) inorganic UV protecting agent consisting of hydrophobic fine particulate metal oxide, the (A) carboxylic acid-modified silicone present in an amount in a range of 5 to 40 parts by mass, the (B) vinyl-based polymer emulsion is present in an amount in a range such that a content of solid content in the emulsion is 0.5 to 10 parts by mass, and the SPF value of the whole cosmetic composition is improved compared to a case where the component (A) and the component (B) are not contained.

3. The oil-in-water emulsion cosmetic composition according to claim 1, wherein the (A) carboxylic acid-modified silicone is in a liquid form at room temperature (25° C.).

4. The oil-in-water emulsion cosmetic composition according to claim 1, wherein a/b is in a range of 0.5 to 2.0.

5. The oil-in-water emulsion cosmetic composition according to claim 1, wherein the (A) carboxylic acid-modified silicone is contained in a range of 0.5% to 15% by mass with respect to a total mass of the cosmetic composition.

6. The oil-in-water emulsion cosmetic composition according to claim 1, wherein the (B) vinyl-based polymer emulsion is an emulsion of an acrylic copolymer polymer obtained by copolymerizing an acrylate ester monomer or a methacrylate monomer.

7. The oil-in-water emulsion cosmetic composition according to claim 1, wherein the (B) vinyl-based polymer emulsion is an emulsion of one or more types of acrylic copolymer polymers selected from the group consisting of:

(b 1) an acrylic acid/alkyl methacrylate copolymer polymer, (b2) an acrylic acid/styrene methacrylate copolymer polymer, and (b3) an acrylic acid/methacrylic acid copolymer polymer having a carbosiloxane dendron structure.

8. The oil-in-water emulsion cosmetic composition according to claim 1, wherein the (D) inorganic UV protecting agent is hydrophobic fine particulate titanium oxide or hydrophobic fine particulate zinc oxide having an average particle size in the range of 1 to 200 nm.

9. The oil-in-water emulsion cosmetic composition according to claim 1, further comprising:

(E) an oil agent.

10. The oil-in-water emulsion cosmetic composition according to claim 9, wherein the (E) oil agent comprises at least one type of UV absorber.

11. The oil-in-water emulsion cosmetic composition according to claim 1, further comprising:

(F) an oil-soluble film forming agent.

12. The oil-in-water emulsion cosmetic composition according to claim 1, further comprising:

(G) polyhydric alcohol.

13. The oil-in-water emulsion cosmetic composition according to claim 1, further comprising:

(H) a water-soluble UV absorber.

14. The oil-in-water emulsion cosmetic composition according to claim 1, which is a sunscreen cosmetic composition.

15. The oil-in-water emulsion cosmetic composition according to claim 1, wherein the (C) basic compound is aminomethyl propanol.

16. The oil-in-water emulsion cosmetic composition according to claim 4, wherein the (C) basic compound is aminomethyl propanol.

* * * * *